(12) United States Patent
Hiei et al.

(10) Patent No.: US 11,136,587 B2
(45) Date of Patent: Oct. 5, 2021

(54) METHOD OF OBTAINING TRANSFORMED PLANT CELL

(71) Applicant: JAPAN TOBACCO INC., Tokyo (JP)

(72) Inventors: Yukoh Hiei, Shizuoka (JP); Toshihiko Komari, Tokyo (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 15/112,343

(22) PCT Filed: Feb. 4, 2015

(86) PCT No.: PCT/JP2015/053137
§ 371 (c)(1),
(2) Date: Jul. 18, 2016

(87) PCT Pub. No.: WO2015/119166
PCT Pub. Date: Aug. 13, 2015

(65) Prior Publication Data
US 2016/0340682 A1    Nov. 24, 2016

(30) Foreign Application Priority Data

Feb. 6, 2014    (WO) .................. PCT/JP2014/052765

(51) Int. Cl.
*C12N 15/82* (2006.01)
*C12Q 1/6895* (2018.01)

(52) U.S. Cl.
CPC ....... *C12N 15/821* (2013.01); *C12N 15/8209* (2013.01); *C12Q 1/6895* (2013.01); *C12N 2830/002* (2013.01); *C12N 2830/003* (2013.01); *C12N 2830/006* (2013.01)

(58) Field of Classification Search
None
See application file for complete search history.

(56) References Cited

U.S. PATENT DOCUMENTS 7,029,908 B1 *  4/2006  Stuiver .............. C12N 15/8205
                                                    435/320.1
2010/0132068 A1   5/2010  Takakura et al.

FOREIGN PATENT DOCUMENTS

| WO | WO 99/01563 A1 | 1/1999 |
|----|----------------|--------|
| WO | WO 03/003816 A2 | 1/2003 |
| WO | WO 2004/092390 A2 | 10/2004 |
| WO | WO 2007/148819 A1 | 12/2007 |
| WO | WO 2010/009353 A1 | 1/2010 |

OTHER PUBLICATIONS

RamanaRao et al. (Plant Cell Rep (2010) 29:473-483). (Year: 2010).*
Batchvarova et al. Theor Appl Genet (1998) 97 :986-989. (Year: 1998).*
Park et al. (Theoretical and applied genetics 109.8 (2004): 1562-1567). (Year: 2004).*
Holme et al. "Transformation of barley (*Hordeum vulgare* L.) by Agrobacterium tumefaciens infection of in vitro cultured ovules." Transgenic plants. Humana Press, 2012. 151-161. (Year: 2012).*
Burgess et al., "A novel, two-component system for cell lethality and its use in engineering nuclear male-sterility in plants," The Plant Journal, vol. 31, No. 1, 2002, pp. 113-125.
Butaye et al., "Approaches to minimize variation of transgene expression in plants," Molecular Breeding, vol. 16, 2005, pp. 79-91.
Chilton et al., "Agrobacterium tumefaciens DNA and PS8 Bacteriophage DNA Not-Detected in Crown Gall Tumors," Proceedings of the National Academy of Sciences, vol. 71, No. 9, Sep. 1974, pp. 3672-3676.
De Buck et al., "Generation of Single-Copy T-DNA Transformants in *Arabidopsis* by the CRE/loxP Recombination-Mediated Resolution System," Plant Physiology, vol. 145, Dec. 2007, pp. 1171-1182.
Dutt et al., "Co-transformation of Grapevine Somatic Embryos to Produce Transgenic Plants Free of Marker Genes," Transgenic Plants: Methods and Protocols, Methods in Molecular Biology, vol. 847, 2012, pp. 201-213.
Eamens et al., "RNA Silencing in Plants: Yesterday, Today, and Tomorrow," Plant Physiology, vol. 147, Jun. 2008, pp. 456-468.
English translation of the Written Opinion of the International Searching Authority (Form PCT/ISA/237) issued in International Application No. PCT/JP2015/053137 dated Apr. 28, 2015.
Extended European Search Report issued in European Application No. 15745845.6 dated Aug. 18, 2017.
Gallego et al., "Positive-negative selection and T-DNA stability in *Arabidopsis* transformation," Plant Molecular Biology, vol. 39, 1999, pp. 83-93.
Hiei et al., "Improved protocols for transformation of indica rice mediated by Agrobacterium tumefaciens," Plant Cell, Tissue and Organ Culture, vol. 85, 2006, pp. 271-283.
International Search Report (Form PCT/ISA/210) issued in International Application No. PCT/JP2015/053137 dated Apr. 28, 2015.
Ishida et al., "Agrobacterium-mediated transformation of maize," Nature Protocols, vol. 2, No. 7, 2007 (published online Jun. 21, 2007), pp. 1614-1621.

(Continued)

*Primary Examiner* — Charles Logsdon
(74) *Attorney, Agent, or Firm* — Birch, Stewart, Kolasch & Birch, LLP

(57) ABSTRACT

The present invention relates to a method of obtaining a transformed plant cell. The present invention comprises the steps of:
(a) co-transforming an intended DNA and a first marker gene into a plant cell; and
(b) selecting from the transformed cells obtained in the step (a), a transformed plant cell wherein the intended DNA is introduced into a chromosome thereof, and the first marker gene is not introduced,
wherein the method does not contain a step to exclude a transformed cell with only the intended DNA introduced into the chromosome by positive selection using the first marker gene.

4 Claims, 9 Drawing Sheets
Specification includes a Sequence Listing.

(56) References Cited

OTHER PUBLICATIONS

Ishida et al., "High efficiency transformation of maize (Zea mays L.) mediated by Agrobacterium tumefaciens," Nature Biotechnology, vol. 14, Jun. 1996, pp. 745-750.
Klein, "Particle Bombardment: An Established Weapon in the Arsenal of Plant Biotechnologists," Plant Transformation Technologies, 2011 (published online Mar. 16, 2011), pp. 53-71.
Kohli et al., "Transgene organization in rice engineered through direct DNA transfer supports a two-phase integration mechanism mediated by the establishment of integration hot spots," Proceedings of the National Academy of Sciences, vol. 95, Jun. 1998, pp. 7203-7208.
Komari et al., "Vectors carrying two separate T-DNAs for co-transformation of higher plants mediated by Agrobacterium tumefaciens and segregation of transformants free from selection markers," The Plant Journal, vol. 10, No. 1, 1996, pp. 165-174.
Kondrák et al., "Generation of Marker- and Backbone-Free Transgenic Potatoes by Site-Specific Recombination . . . Marker Gene in a Non-Regular One-Border Agrobacterium Transformation Vector," Transgenic Research, vol. 15, No. 6, Dec. 2006 (published online Oct. 27, 2006), pp. 729-737.
Li et al., "Optimizing Agrobacterium-Mediated Transformation of Grapevine," In Vitro Cellular & Developmental Biology—Plant, vol. 42, 2006, pp. 1-8.
Nagaya et al., "Expression of Randomly Integrated Single Complete Copy Transgenes Does not Vary in Arabidopsis thaliana," Plant Cell Physiology, vol. 46, No. 3, 2005, pp. 438-444.
Oltmanns et al., "Generation of Backbone-Free, Low Transgene Copy Plants by Launching T-DNA from the Agrobacterium Chromosome," Plant Physiology, Mar. 2010, vol. 152, pp. 1158-1166.
Park et al., "Co-transformation using a negative selectable marker gene for the production of selectable marker gene-free transgenic plants," Theoretical and Applied Genetics, vol. 109, 2004 (published online Sep. 22, 2004), pp. 1562-1567.
Ramanarao et al., "Selectable marker elimination in the T0 generation by Agrobacterium-mediated . . . non-conditional negative selectable marker and bar for transient positive selection," Plant Cell Reports, vol. 29, 2010 (published online Mar. 5, 2010), pp. 473-483.
Register III et al., "Structure and function of selectable and non-selectable transgenes in maize after introduction by particle bombardment," Plant Molecular Biology, vol. 25, 1994, pp. 951-961.
Rommens et al., "Crop Improvement through Modification of the Plant's Own Genome," Plant Physiology, vol. 135, May 2004, pp. 421-431.
Shou et al., "Assessment of transgenic maize events produced by particle bombardment or Agrobacterium-mediated transformation," Molecular Breeding, vol. 13, 2004, pp. 201-208.
Srivastava et al., "Single-copy primary transformants of maize obtained through the co-introduction of a recombinase-expressing construct," Plant Molecular Biology, vol. 46, 2001, pp. 561-566.
Srivastava et al., "Single-copy transgenic wheat generated through the resolution of complex integration patterns," Proceedings of the National Academy of Science, vol. 96, Sep. 1999, pp. 11117-11121.
Terada et al., "Efficient gene targeting by homologous recombination in rice," Nature Biotechnology, vol. 20, Oct. 2002 (published online Sep. 9, 2002), pp. 1030-1034.
Upadhyaya et al., "An update on the progress towards the development of marker-free transgenic plants," Botanical Studies, vol. 51, 2010, pp. 277-292.
Wang et al., "High-efficiency silencing of a β-glucuronidase gene in rice is correlated with repetitive transgene structure but is independent of DNA methylation," Plant Molecular Biology, vol. 43, 2000, pp. 67-82.
Yang et al., "Estimating the copy number of transgenes in transformed rice by real-time quantitative PCR," Plant Cell Reports, vol. 23, 2005 (published online Oct. 1, 2004), pp. 759-763.
Yau et al., "Less is more: strategies to remove marker genes from transgenic plants," BMC Biotechnology, vol. 13, No. 36, 2013, pp. 1-23.
Ye et al., "Enhanced production of single copy backbone-free transgenic plants in multiple crop species using binary vectors with a pRi replication origin in Agrobacterium tumefaciens," Transgenic Research, vol. 20, 2011 (published online Nov. 2, 2010), pp. 773-786.

* cited by examiner a.

b.

c.

METHOD OF OBTAINING TRANSFORMED PLANT CELL

TECHNICAL FIELD

The present invention relates to a method of obtaining a transformed plant cell and a method of producing a transformed plant.

REFERENCE TO SEQUENCE LISTING SUBMITTED VIA EFS-WEB

This application includes an electronically submitted sequence listing in .txt format. The .txt file contains a sequence listing entitled "2016-12-12 SequenceListing 0230-0339PUS1.txt" created on Dec. 9, 2016 and is 6,743 bytes in size. The sequence listing contained in this .txt file is part of the specification and is hereby incorporated by reference herein in its entirety.

BACKGROUND ART

Transformation of Plant

In transforming a plant, a technique of introducing a DNA into a plant cell, which allows a foreign gene to be retained/expressed in progenies of fertile seeds or vegetative propagated plants, is employed. Quite a few monocotyledons and dicotyledons have been actually transformed by using the technique.

In the field of plant physiology and plant molecular biology, the transformants of *Arabidopsis thaliana*, rice, Brachypodium and the like are often utilized for basic research. Transformants of crops such as maize, rice, wheat, barley, sorghum, soybean, rapeseed, sunflower, cotton, potato and tomato as well as fruits and other vegetables have been produced. Besides, since a high-value added trait can be provided by the transformation, a strong interest exists for the commercial use, and transformed maize, soybean, rapeseed and cotton are widely commercially produced at present.

There is, however, a serious problem in both aspects of research and commercial use in production of transformed plants. The problem is that a created transformant frequently has a multicopy target DNA. In transformed plants containing a target DNA introduced at a high copy number, the expression level of the introduced gene is largely varied among plants, and a plant in which the expression of the introduced gene is strongly inhibited, which phenomenon is designated as homology-dependent gene silencing, is included in not a few cases. On the other hand, a transformant containing only a single copy of the target DNA shows stable gene expression regardless of the insertion position on the genome (Nagaya et al., 2005). There are two types of the homology-dependent gene silencing, that is, post-transcriptional gene silencing (PTGS) and transcriptional gene silencing (TGS), both of which are caused via a double stranded RNA, and the PTGS is easily caused in the case where multiple copies of a target DNA linked to one another in a forward or reverse direction are introduced, or in the case where a partially deleted target DNA is introduced together. The TGS is caused by epigenetics, and is usually accompanied by methylation of a DNA via a small RNA homologous to a promoter region upstream of the gene. The methylation is retained even through mitosis or meiosis, and as a result, the silencing is inherited to progeny (Eamens et al., 2008).

Furthermore, the aspect of the integration of a targetDNA into a genome is more complicated and more difficult to analyze as the copy number is higher. Accordingly, a target DNA is introduced preferably at a copy number of 1 to 2, and most preferably as a single copy for most purposes of the transformation, such as purposes of 1) evaluating the effect of an introduced gene in a transformant based on the expression level, 2) evaluating a characteristic of a promoter or a transcription factor in a transformant, 3) producing a T-DNA tagging library, and 4) producing a transformed plant for commercialization.

As a transformation method for plants, physicochemical methods (methods for direct introduction of DNA) such as a particle-gun method, an electroporation method, an electro-injection method, a polyethylene-glycol method and a whisker method, as well as biological methods using the function of bacteria belonging to genus *Agrobacterium* (methods for indirect introduction of DNA) are known. The direct introduction is often associated with problems such as fragmentation of the targetDNA during introduction, and introduction of a high number of copies (which is as high as 100 copies in worst cases) (Butaye et al., 2005). Besides, in the case where the target DNA is introduced at a high copy number, the copies are often linked to one another to be integrated into the same locus (Kohli et al., 1998; Klein, 2010). As a result, there is a frequent occurrence of a transformant showing the gene silencing in which the target gene is not expressed (Register et al., 1994).

In the *Agrobacterium*-mediated method, the target DNA is introduced via expression control of gene culsters in the virulent region (vir region) of Ti or Ri plasmids. The target DNA is introduced by the work of protein clusters encoded in the vir genes through many processes including recognition of the interaction and signaling between plant cells and bacteria, induction of expression of the vir genes, creation of Type IV secretion route, recognition of T-DNA border repeat sequences, formation of T-DNA strands, transfer of the T-DNA strands to plant cells and then to nuclei, and integration of the T-DNA into the plant nucleus genome. Therefore, this method restrains the number of introduced copies of the target DNA (to less than 10 copies) and fragmentation during the introduction are not often (Shou et al., 2004; Butaye et al. 2005). Although the *Agrobacterium*-mediated method is thus a superior transformation method to the direct introduction of DNA, the copy number of DNA to be introduced into a genome still cannot be sufficiently controlled. Besides, it is not unusual that multiple copies of a DNA are introduced into the same locus (Wang and Waterhouse, 2000). Accordingly, there arises a difference to some extent in the expression level of the targetgene among transformed plants, and a transformed plant showing the homology-dependent gene silencing may be produced (Butaye et al., 2005; Nagaya et al., 2005).

Attempts to Control the Copy Number of Introduced DNA

Due to such background arts, there are several reports on methods for introducing a target DNA at a low copy number. One of these methods is a method using a site-specific recombination system. First, a DNA fragment having a recognition sequence (lox) of a site-specific recombination enzyme in a reverse direction on both sides of an intended DNA having a selectable marker is introduced into a plant. Besides, a Cre-expression cassette is precedently introduced into another plant. Next, a T0 plant in which multiple linked copies of the targetDNA are introduced is crossed with a T0 plant expressing Cre. In the thus obtained F1 plant, when Cre is expressed, merely DNA regions each sandwiched between the lox sequences in the forward direction inside the DNA regions are all cut out from the DNA region where the multiple linked copies are introduced. As a result, both ends remaining in the DNA are linked to each other, and a cell containing merely a single copy of the target DNA is obtained. When this cell is differentiated into germ cells, F2 plants containing the DNA of interest as a single copy or single copy homozygous can be obtained (Srivastava et al., 1999; De Buck et al., 2007). The method employing the cross has, however, a serious disadvantage that it takes a long time to obtain an intended plant. Further, if epigenetic TGS is caused, even though the copy number is reduced through the Cre-lox recombination, the expression of the intended DNA remains suppressed.

Furthermore, as a method similarly using a site-specific recombination system, a method of co-transforming a target DNA fragment and a DNA fragment having a Cre gene has been reported (Srivastava and Ow, 2001). When the co-transformed Cre is expressed, a region sandwiched between the lox sequences is cut out from a region where multiple linked copies of the target DNA are introduced, and a plant containing a single copy of the target DNA can be obtained for T0 generation. In this co-transformation method, however, if the Cre gene itself is introduced at a high copy number, it cannot function due to expression inhibition in some cases. According to a review by Butaye et al., (2005), a method of reducing the copy number by using a site-specific recombination system is theoretically possible, but there are merely a few successful reports, and the transformation efficiency is also low. Incidentally, it is also cited that this method has a problem in which a wild-type genome region sandwiched between two introduced copies of DNA is cut out and deleted (Butaye et al., 2005).

A second of these methods is a method using, oriRi of *Agrobacterium rhizogenes* as the origin of replication of a vector having a T-DNA of a target DNA in the *Agrobacterium*-mediated method. By using a binary vector in which oriRi functions and a binary vector in which oriV, that is, an IncP RK-2 origin of replication, functions, Ye et al., (2011) compared the frequency of plants in which a target DNA is introduced as a single copy without containing a backbone sequence of a vector corresponding to the outside of a T-DNA in an obtained transformant. The frequency of single copy transgenic plants obtained by using the oriRi vector was 38% to 40% in transformed soybean plants, which is double as compared with that obtained by using the oriV vector, was 51% in transformed rapeseed plants, which is 1.5 times as high, and was 58% in transformed maize plants, which is 1.4 times as high. On the other hand, the transformation efficiency was lowered, and assuming that the efficiency attained by using the oriV vector is 100%, it was 45% to 68% for soybean, 80% for rapeseed and 58% for maize (Ye et al., 2011). Production efficiency per tested material obtained in consideration of the production frequency of a backbone-free single copy transformant by using the oriRi vector as well as the transformation efficiency was, as compared with that attained by using the oriV vector, 0.96 to 1.36 times as high for soybean, 1.2 times as high for rapeseed, and 0.82 time as high for maize. Even if the production efficiency per tested material is low, it can be said that the oriRi binary vector can be recognized as useful as long as the work efficiency and the cost efficiency are high as a whole. In the analysis of a transformant, much cost and labor are required for the extraction of DNA and the analysis of the copy number, and hence, it seems that the oriRi binary vector is useful for improving the whole efficiency.

A third of these methods is a method in which plant transformation is performed with a T-DNA held on the chromosome of *Agrobacterium*. Oltmanns et al., (2010) integrated, by homologous recombination, a DNA region including a T-DNA into a picA region on the chromosome of each of the GV3101 strain and the EHA101 strain of *agrobacterium*, and used the resultant for the transformation of maize. Then, they examined the frequency of single copy transgenic plants in the thus obtained transformants. As a result, the frequency of the single copy transgenic plants in the transformed maize plants was extremely high as 64% in using the EHA101 strain and 58% in using the GV3010 strain (Oltmanns et al., 2010). This method in which a T-DNA is held on the chromosome of *Agrobacterium* has, however, a fundamental problem of low transformation efficiency, and the transformation efficiency of maize was about 1% in using either of the EHA101 strain and the GV3010 strain (Oltmanns et al., 2010). Incidentally, the transformation efficiency attained by the conventional method using a binary vector and an *Agrobacterium* strain is 9-12% when using the EHA101 strain and 5-8% in using the GV3101 strain. This method in which a T-DNA is held on the chromosome of *Agrobacterium* seems to be rather effective merely when a floral dip method for *Arabidopsis thaliana* using the GV3010 strain is employed. The transformation efficiency was 0.9%, which is not largely lower than 1.6-2.1% attained by the conventional method, and the frequency of single copy transgenic plants was extremely high as 80% while that attained by the conventional method is 16 to 35% (Oltmanns et al., 2010). If this method is applied to the EHA101 strain having the same chromosome background, however, the transformation efficiency was about 0.1%, which is about 1/10 of that attained by the conventional method (Oltmanns et al., 2010). As described so far, various attempts to reduce the copy number of an introduced DNA have been made, but these methods respectively have their disadvantages and cannot be widely used as an effective method.

Co-Transformation

The co-transformation of a foreign DNA in a plant is usually employed for obtaining a transformant in which only the target DNA is introduced. Selectable marker genes and selectable drugs are very useful tools for obtaining transformed cells from plant tissues mostly containing non-transformed cells, but are basically unnecessary after obtaining transformants. In the *Agrobacterium*-mediated method, the co-transformation is performed mainly for purpose of excluding a selectable marker gene in the next generation. That is, a target foreign DNA and a selectable marker gene are inserted respectively on different T-DNAs, and the resultants are simultaneously introduced into a plant cell by using *Agrobacterium*. When a cell clump selected by a selectable drug is regenerated, a transformant in which the target DNA is introduced together with the selectable marker gene is obtained. If the target DNA and the selectable marker gene are introduced on the different chromosomes, a plant that has the target DNA but has the selectable marker gene eliminated can be obtained in the next generation by genetic segregation (Yau and Stewart, 2013). Besides, the co-transformation method mediated by *Agrobacterium* is divided into the following four types: A type in which two T-DNAs are separately located on two binary vectors in one strain; a type in which two T-DNAs are located on one binary vector in one strain; a type in which two T-DNAs are separately located respectively on binary vectors of two strains and the strains are mixedly inoculated, and a type in which two right border sequences are located on one binary vector of one strain (Yau and Stewart, 2013).

Besides, the co-transformation method is employed in the direct introduction of DNA not for purpose of eliminating a selectable marker gene but for purpose of saving a preliminary operation of linking a target DNA to a selectable marker gene before gene introduction. This is because, as described above, a plurality of foreign DNAs are easily integrated into the same locus in the direct introduction of DNA. Actually, even if the co-transformation method is employed for purpose of eliminating a selectable marker gene in the direct introduction of DNA, the efficiency of eliminating the selectable marker gene in the next generation is extremely low (Yau and Steward, 2013).

When the co-transformation is used, after selecting T0 plants by expression of a positive selectable marker gene such as a hygromycin resistance gene, if the selection is performed also by using a positive selectable marker in T1 generation, T1 plants, which are obtained by the gene segregation and in which only a targetDNA is introduced, cannot be selected because they are withered and killed by hygromycin. Accordingly, a method of assaying the drug resistance not in a whole plant but in a leaf segment and/or a method of assaying an introduced DNA by PCR or the like are necessary. These assays require, however, labor. In order to reduce the labor, a method using positive-negative selection is effective. As selectable markers, not only a positive selectable marker gene but also a negative selectable marker gene are located on the same T-DNA, and after obtaining transformants in T0 generation by positive selection, negative selection is performed in T1 generation to wither and kill T1 plants in which the selectable marker gene is introduced. Surviving T1 plants no longer contain the selectable marker gene, and it can be simply discriminated by the PCR or gene expression whether or not the target DNA is contained (Yau and Stewart, 2013).

An attempt to eliminate a selectable marker gene in T0 generation, which is valuable for vegetatively propagated crops, by the co-transformation method mediated by *Agrobacterium* has been made. For the introduction, two types of T-DNA, that is, an "intended DNA" and a "positive selectable marker gene-negative selectable marker gene", are used. There are two reports, both of which describe methods having low efficiency and including similar steps (Dutt et al., 2008; Ramana Rao and Veluthambi, 2010). That is, after cocultivation, at a stage where an intended DNA and selectable markers have not been integrated into the chromosome and a positive selectable marker is transiently expressed, positive selection by using a drug is performed for selecting cells. In this process, cells containing the intended DNA and not containing the selectable marker genes are excluded, but the selected cells include a cell where the intended DNA is introduced together. Thereafter, the resultant tissue is transferred to a medium free of a selectable drug, and thus, a cell clump in which the intended DNA has been integrated into the chromosome but the selectable marker has not been integrated into the chromosome is obtained. On the other hand, a cell in which the selectable marker gene has been integrated into the chromosome thereafter dies due to the expression of a negative selectable marker. The thus obtained cell clump including only the intended DNA is regenerated to obtain a target plant.

In the above-described method, Dutt et al., (2008) obtained, by using a large number of (specific number not mentioned) somatic embryos of grape, five plants in which only an intended DNA of egfp (enhanced green fluorescent protein) was introduced. Dutt et al., (2008) describes that they have found, as a result of analysis by real time PCR, that the copy number of the egfp gene introduced into each of the five plants was single copy in three plants, two copies in one plant, and six copies in one plant. Since the ratio of the plants containing a single copy of the introduced gene is 60%, the efficiency seems to be high, but it is reported that a ratio of single copy transformants was also 60% in transformed grape plants obtained by a general transformation method by the same research group (Li et al., 2006). In a result obtained by Ramana Rao and Veluthambi (2010) by using tobacco, merely five plants out of obtained 114 plants had nptII (neomycin phosphotransferase II) of an intended DNA. The most significant process of these methods is the positive selection at the stage of transient expression. If this process is not conducted, cells in which both genes are introduced and transiently expressed cannot be concentrated, and a resultant tissue is in a chimeric state mainly occupied by cells in which none is introduced, and hence it is extremely difficult to obtain a target plant.

CITATION LIST

Patent Literature

Patent Document 1: WO2007/148819 A1

Non Patent Document

Non Patent Document 1: Burgess, D. G., Ralston, E. J., Hanson, W. G., Heckert, M., Ho, M., Jenq, T., Palys, J. M., Tang, K., and Gutterson, N. (2002). A novel, two-component system for cell lethality and its use in engineering nuclear male-sterility in plants. Plant J 31, 113-125.

Non Patent Document 2: Butaye, K. M. J., Cammue, B. P. A., Delaure, S. L., and De Bolle, M. F. C. (2005). Approaches to Minimize Variation of Transgene Expression in Plants. Molecular Breeding 16, 79-91.

Non Patent Document 3: Chilton, M.-D., Currier, T. C., Farrand, S. K., Bendich, A. J., Gordon, M. P., and Nester, E. W. (1974). *Agrobacterium tumefaciens* DNA and PS8 bacteriophage DNA not detected in crown gall tumors. Proc Natl Acad Sci USA 71, 3672-3676.

Non Patent Document 4: De Buck, S., Peck, I., De Wilde, C., Marjanac, G., Nolf, J., De Paepe, A., and Depicker, A. (2007). Generation of single-copy T-DNA transformants in *Arabidopsis* by the CRE/loxP recombination-mediated resolution system. Plant Physiol 145, 1171-1182.

Non Patent Document 5: Dutt, M., Li, Z. T., Dhekney, S. A., and Gray, D. J. (2008). Co-transformation of grapevine somatic embryos to produce transgenic plants free of marker genes. Methods Mol Biol 847, 201-213.

Non Patent Document 6: Eamens, A., Wang, M. B., Smith, N. A., and Waterhouse, P. M. (2008). RNA silencing in plants: yesterday, today, and tomorrow. Plant Physiol 147, 456-468.

Non Patent Document 7: Hiei, Y., and Komari, T. (2006). Improved protocols for transformation of indica rice mediated by *Agrobacterium tumefaciens*. Plant Cell, Tissue and Organ Cul 85, 271-283.

Non Patent Document 8: Klein, T. M. (2010). Particle Bombardment: An Established Weapon in the Arsenal of Plant Biotechnologists. In Plant Transformation Technologies (Wiley-Blackwell), pp. 51-71.

Non Patent Document 9: Kohli, A., Leech, M., Vain, P., Laurie, D. A., and Christou, P. (1998). Transgene organization in rice engineered through direct DNA transfer supports a two-phase integration mechanism mediated by the establishment of integration hot spots. Proc Natl Acad Sci 95, 7203-7208.

Non Patent Document 10: Komari, T., Hiei, Y., Saito, Y., Murai, N., and Kumashiro, T. (1996). Vectors carrying two separate T-DNAs for co-transformation of higher plants mediated by *Agrobacterium tumefaciens* and segregation of transformants free from selection markers. Plant J 10, 165-174.

Non Patent Document 11: Li, Z. T., Dhekney, S., Dutt, M., Aman, M., Tattersall, J., Kelley, K. T., and Gray, D. J. (2006). Optimizing *Agrobacterium*-mediated transformation of grapevine. In Vitro Cell Dev Biol—Plant 42, 220-227.

Non Patent Document 12: Nagaya, S., Kato, K., Ninomiya, Y., Horie, R., Sekine, M., Yoshida, K., and Shinmyo, A. (2005). Expression of randomly integrated single complete copy transgenes does not vary in *Arabidopsis thaliana*. Plant Cell Physiol 46, 438-444.

Non Patent Document 13: Oltmanns, H., Frame, B., Lee, L.-Y., Johnson, S., Li, B., Wang, K., and Gelvin, S. B. (2010). Generation of Backbone-Free, Low Transgene Copy Plants by Launching T-DNA from the *Agrobacterium* Chromosome. Plant Physiol 152, 1158-1166.

Non Patent Document 14: RamanaRao, M., and Veluthambi, K. (2010). Selectable marker elimination in the T0 generation by *Agrobacterium*-mediated co-transformation involving Mungbean yellow mosaic virus TrAP as a non-conditional negative selectable marker and bar for transient positive selection. Plant Cell Rep 29, 473-483.

Non Patent Document 15: Register, J. C. 3rd, Peterson, D. J., Bell, P. J., Bullock, W. P., Evans, I. J., Frame, B., Greenland, A. J., Higgs, N. S., Jepson, I., Jiao, S. et al. (1994). Structure and function of selectable and non-selectable transgenes in maize after introduction by particle bombardment. Plant Mol Biol 25, 951-961.

Non Patent Document 16: Shou, H., Frame, B., Whitham, S., and Wang, K. (2004). Assessment of transgenic maize events produced by particle bombardment or *Agrobacterium*-mediated transformation. Mol Breed 13, 201-208.

Non Patent Document 17: Srivastava, V., and Ow, D. (2001). Single-copy primary transformants of maize obtained through the co-introduction of a recombinase-expressing construct. Plant Mol Biol 46, 561-566.

Non Patent Document 18: Srivastava, V., Anderson, O. D., and Ow, D. W. (1999). Single-copy transgenic wheat generated through the resolution of complex integration patterns. Proceedings of the National Academy of Sciences 96, 11117-11121.

Non Patent Document 19: Terada, R., Urawa, H., Inagaki, Y., Tsugane, K., and Iida, S. (2002). Efficient gene targeting by homologous recombination in rice. Nat Biotechnol 20, 1030-1034.

Non Patent Document 20: Upadhyaya, C. P., Nookaraju, A., Gururani, M. A., Upadhyaya, D. C., Kim, D.-H., Chun, S.-C. and Park, S.-W. (2010). An update on the progress towards the development of marker-free transgenic plants. Botanical Studies p. 277-292

Non Patent Document 21: Wang, M. B., and Waterhouse, P. M. (2000). High-efficiency silencing of a beta-glucuronidase gene in rice is correlated with repetitive transgene structure but is independent of DNA methylation. Plant Mol Biol 43, 67-82.

Non Patent Document 22: Yau, Y. Y., and Stewart, C. N., Jr. (2013). Less is more: strategies to remove marker genes from transgenic plants. BMC Biotechnol 13, 36.

Non Patent Document 23: Ye, X., Williams, E., Shen, J., Johnson, S., Lowe, B., Radke, S., Strickland, S., Esser, J., Petersen, M., and Gilbertson, L. (2011) Enhanced production of single copy backbone-free transgenic plants in multiple crop species using binary vectors with a pRi replication origin in *Agrobacterium tumefaciens*. Transgenic Res 20, 773-786

Non Patent Document 24: Ishida, Y., Hiei, Y., and Komari, T. (2007). *Agrobacterium*-mediated transformation of maize Nat Protocols 2, 1614-1621

Non Patent Document 25: Ishida, Y., Saito, H., Ohta, S., Hiei, Y., Komari, T., and Kumashiro, T. (1996). High efficiency transformation of maize (*Zea mays* L.) mediated by *Agrobacterium tumefaciens*. Nat Biotechnol 14, 745-750

Non Patent Document 26: Yang L., Ding J., Zhang C., Jia J., Weng H., Liu W., and Zhang D. (2005) Estimating the copy number of transgenes in transformed rice by real-time quantitative PCR. Plant Cell Rep 23, 759-763

SUMMARY OF INVENTION

Technical Problem

In a transformed plant in which a target foreign gene is introduced at a high copy number, the phenomenon designated as gene silencing in which the expression of the introduced gene is strongly suppressed often occurs. Furthermore, the aspect of the integration of a target DNA into a genome is more complicated and more difficult to analyze as the copy number is higher. The transformation is performed for purposes of 1) evaluating the effect of an introduced gene in a transformant based on the expression level, 2) evaluating a characteristic of a promoter or a transcription factor in a transformant, 3) producing a T-DNA tagging library, and 4) producing a genetically modified plant for commercialization, and for any purposes, a target DNA is preferably introduced at a copy number of 1 to 2. Most preferably, it is introduced as a single copy.

Accordingly, an object of the present invention is to provide a method of obtaining a transformed plant cell by which the copy number of an intended DNA introduced per cell of the plant is small.

Solution to Problem

The present invention includes, but is not limited to, the following embodiments:

Embodiment 1

A method of obtaining a transformed plant cell, the method comprising the steps of:

(a) co-transforming an intended DNA and a first marker gene into a plant cell; and (b) selecting from the transformed cells obtained in the step (a), a transformed plant cell wherein the intended DNA is introduced into a chromosome thereof, and the first marker gene is not introduced, wherein the method does not contain a step to exclude a transformed cell with only the intended DNA introduced into the chromosome by positive selection using the first marker gene.

Embodiment 2

The method according to Embodiment 1, wherein the first marker gene is a negative selectable marker gene.

Embodiment 3

The method according to any one of Embodiments 1 and 2, wherein a blend ratio of the intended DNA and the first marker gene used for co-transformation in the step (a) is between 3:1-1:5.

Embodiment 4

The method according to any one of Embodiments 1-3, wherein
a positive selectable marker gene, which is a second marker gene, is linked to the intended DNA used in the step (a),
the selection of the transformed cells with the intended DNA introduced into a chromosome in the step (b) is conducted by a positive selection using the second marker gene.

Embodiment 5

The method according to any one of Claims 1-4, wherein the step (a) is conducted by a transformation method selected from a group consisting of an Agrobacterium-mediated method, a particle-gun method, an electroporation method, an electro-injection method, a polyethylene-glycol method and a whisker method.

Embodiment 6

A method of producing a transformed plant, the method comprising
obtaining a transformed plant cell by the method described in any one of Embodiments 1-5;
culturing the plant cell to obtain a plant.

Embodiment 7

A method of transforming a plant, the method comprising the steps of
(a) co-transforming an intended DNA and a first marker gene into a plant cell; and
(b) selecting from the transformed cells obtained in the step (a), a transformed plant cell wherein the intended DNA is introduced into a chromosome thereof, and the first marker gene is not introduced,
wherein the method does not contain a step to exclude a transformed cell with only the intended DNA introduced into the chromosome by positive selection using the first marker gene.

Advantageous Effects of Invention

The method of the present invention is a technique by which a cell in which a target DNA is introduced at a high copy number can be eliminated at an initial stage of a transformation system. When the present invention is employed, a transformed plant in which merely a single copy of a target DNA is introduced can be preferably obtained at a frequency 1.3 or more times as high as that attained by the conventional technique. Besides, the frequency of transformants in which three or more copies are introduced can be preferably reduced to ½ or less of that attained by the conventional technique. If the technique of the present invention is applied to a known plant transformation technique, the copy number of a target DNA in a resultant transformed plant can be reduced. Furthermore, if the method of the present invention is used together with a conventional method of reducing the copy number, a transformed plant in which merely a single copy is introduced can be obtained at a higher frequency.

DESCRIPTION OF EMBODIMENTS

Figure 1:
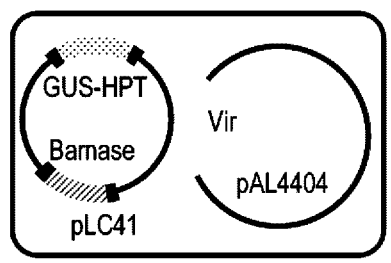
FIG. 1 is a schematic diagram of co-transformation methods employing an *Agrobacterium*-mediated method used in a technique for eliminating a multicopy transgenic cell, in which a. illustrates a one-strain one-vector method, LBA4404 (pLC41 GUS-HPT cotra. Barnase), b. illustrates a two-strain mixed method, LBA4404 (pLC41 GUS-HPT)+LBA4404 (pLC41 Barnase), and c. illustrates a one-strain two-vector method (ternary vector system), LBA4404 (pLC41 GUS-HPT::pGW Barnase), in which GUS-HPT: a T-DNA having an intron-mediated GUS gene and an HPT gene, Barnase: a T-DNA having an intron-mediated Barnase gene, Vir: a virulence region, and pAL4404: a disarmed Ti plasmid.
Figure 1:
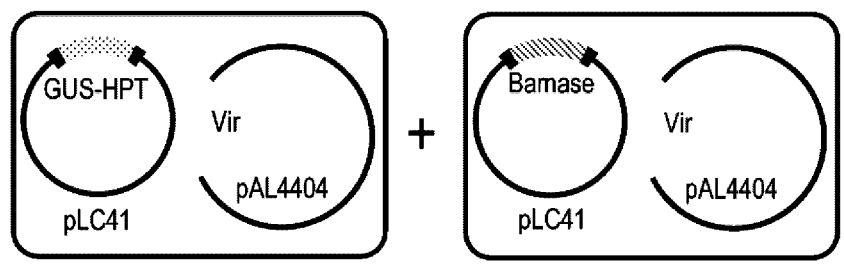
Figure 1:
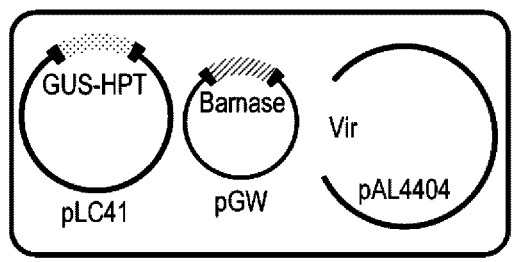

Preferred embodiments for practicing the present invention will now be described.

The present invention relates to a method of obtaining a transformed plant cell. The method of the present invention comprises the steps of:

(a) co-transforming an intended DNA and a first marker gene into a plant cell; and (b) selecting from the transformed cells obtained in the step (a), a transformed plant cell wherein the intended DNA is introduced into a chromosome thereof, and the first marker gene is not introduced, wherein the method does not contain a step to exclude a transformed cell with only the intended DNA introduced into the chromosome by positive selection using the first marker gene.

Plant

A plant for which the method of the present invention is employed is not especially limited, but the plant includes arbitrary plants such as algae, angiosperms and gymnosperms, and may be a monocotyledon or a dicotyledon. A tissue to be tested for transformation can be appropriately selected in accordance with the type of plant or a transformation method to be employed.

Marker Gene

The present invention includes the step (a) of co-transforming an intended DNA and a first marker gene into a plant cell. The term "marker gene" as used herein means a gene having a property to work as an index to be used for selecting a cell having the gene introduced therein or a cell not having the gene introduced therein.

Not intending to be bound by the theory, if the intended DNA and the first marker gene are co-transformed, it is presumed that the intended DNA and the first marker gene are randomly introduced into a genome while mixedly present in a cell nucleus. As a result of such transformation, "cells in which the gene is introduced at a low copy number" and "cells in which the gene is introduced at a high copy number" are produced, and there is a low possibility that a "cell in which only the intended DNA is introduced at a high copy number" is produced as the latter cells, but many of the latter cells are "multicopy transgenic cells containing both the intended DNA and the marker gene". Accordingly, if "cells in which the intended DNA is introduced but the marker gene is not introduced" are selected from a resultant group of transformed cells, the number of "cells in which the intended DNA is introduced at a high copy number" can be largely reduced.

Accordingly, the "first marker gene" of the present invention refers to a gene different from the intended DNA and may have a property capable of excluding a marker gene expressing cell when expressed in a cell. That is, it may be a gene that can exclude a cell which expresses the marker gene ("a marker gene expressing cell") depending on the presence of expression of an easily detectable gene having been introduced as a selection index. In the present invention, negative selection refers to selective exclusion of a cell in which the marker gene is expressed. Accordingly, in other words, the first marker gene may have a property capable of the negative selection.

If a marker gene expressing cell and a cell in which the marker gene is not introduced can be visually discriminated from each other, the cell can be artificially excluded from a cell group by using a tool such as tweezers or a knife, for example, under a microscope. Examples of such a marker gene include fluorescent protein genes of a green fluorescent protein (GFP), a red fluorescent protein (DsRed), a luciferase gene and the like, and a gene of an enzyme catalyzing a color reaction, such as a lacZ gene.

Besides, drug resistance genes such as a hygromycin resistance gene, a gentamicin resistance gene, a kanamycin resistance gene, an ampicillin resistance gene, a spectinomycin resistance gene, a tetracycline resistance gene, a bialaphos resistance gene, and a glyphosate resistance gene can be used as such a marker gene. If the concentration of a drug used for supplementing a selection medium in a drug selection step is limited below an extent where cells not containing a drug resistance gene are not killed, a cell not containing the drug resistance gene is not killed but is minimally proliferated, and thus the appearance of such a cell becomes different from that of a normal cell, and therefore, the cell can be discriminated from a drug resistance gene transgenic cell.

Thus, a gene enabling visual discrimination of a cell, such as a gene of an enzyme catalyzing a color reaction, or a drug resistance gene also has the property capable of the negative selection, and hence can be used as the first marker gene of the present invention.

Besides, as the "first marker gene" of the present invention, a negative selectable marker gene can be suitably used. Herein, a marker gene having a property to selectively eliminate a cell containing the gene itself when expressed is designated as the negative selectable marker gene. In addition, it also includes a gene whose property to selectively eliminate a cell containing the gene itself functions if a specific substance is added to a plant cell or a medium. Furthermore, the negative selectable marker gene is not necessarily limited to a structural gene, but a nonstructural gene different from a structural gene encoding a protein, such as an expressed sequence of a non-coding RNA, can be used. The negative selectable marker gene induces cell death, cell growth arrest or abnormal tissue formation when the gene is integrated into a plant genome and expressed in a period from the gene transfer process up to the regeneration of a plant. If a cell death inducing negative selectable marker gene is used as the marker gene, marker gene expressing cells die out, and therefore, there is no need to perform an operation for excluding the marker gene expressing cells, which largely improves the work efficiency.

It is preferable that the negative selectable marker gene does not remain in a regenerated plant. Those skilled in the art can appropriately select such a negative selectable marker gene. Besides, the expression of the negative selectable marker gene is preferably at a level where cell death is not induced at a stage of transient expression. In the co-transformation step of the present invention, cells in which only the target DNA is integrated into the genome and the negative selectable marker gene is transiently expressed can be produced, but part of these cells are changed, through cultivation, to a cell containing only the target DNA. Accordingly, from the viewpoint of preventing the transformation efficiency from lowering, it is preferable that these cells are not killed by the transient expression of the negative selectable marker gene. For example, if the negative selectable marker is highly toxic, the toxicity is preferably suppressed by, for example, applying a promoter for reducing the expression of the marker gene. Such expression control can be appropriately conducted on the basis of a technique known to those skilled in the art. Further, although without any limitation, an example of the present invention describes below that a nos promoter was suitably used when a Barnase gene was used as the negative selectable marker gene.

A negative selectable marker gene most widely used for plants is the codA gene from $E.$ $coli$ (Yau and Stewart, 2013). The codA gene encodes cytosine deaminase, and converts 5-fluorocytosine (5-FC) having no toxicity into 5-fluorouracil (5-FU) having toxicity. The argE of the ornithine deacetylase gene from $E.$ $coli$ converts N-acetyl-phosphinothricin (N-acetyl-PPT) not toxic to plants into phosphinothricin (PPT) having a herbicidal activity.

Cytochrome P450sui of bacteria converts a non-toxic herbicide R4702 precursor into cytotoxic herbicide R4702. Diphtheria toxin fragment A (DT-A) is toxic to plant cells but is not toxic to *E. coli* and *Agrobacterium* (Terada et al., 2002). Besides, since the DT-A gene does not contain a poly-A signal, an mRNA transiently expressed is decomposed at once, and if integrated into a genome, it is continuously expressed by using a nearby poly-A signal. Barnase is a ribonuclease derived from *Bacillus amyloliquefaciens*. It is strongly toxic to both a prokaryote and a eukaryote, but the toxicity to a prokaryote can be suppressed by interposing an intron in the gene (Burgess et al., 2002). Without any limitation, in the method of the present invention, such a gene can be suitably used as the negative selectable marker gene.

Further, the steps of the present invention do not contain a step to exclude a transformed cell with only the intended DNA introduced into the chromosome by positive selection using the first marker gene. The definition of the positive selection will be described in detail in an item of "Second Marker Gene", and if the positive selection is conducted by using the first marker gene, a transformed cell in which only the intended DNA is introduced into the chromosome is excluded, and hence, the effects of the present invention cannot be attained.

In the method of the present invention, the number of first marker genes to be used is not limited. Preferably, one or two marker genes can be suitably used.

Intended DNA

The "intended DNA" is an arbitrary DNA to be introduced into a cell, and is not especially limited. The intended DNA is a DNA to be introduced into the chromosome (genome) of the plant cell, and is not necessarily limited to a structural gene, but a nonstructural gene different from a structural gene encoding a protein can be used. The "intended DNA" may be linked to intended promoter and terminator. As the "intended DNA", one having an arbitrary length in accordance with the transformation method to be employed can be used. For example, if the *Agrobacterium*-mediated method is employed, one having a length of 0.1 kb to 50 kb is suitably used, which does not limit the present invention.

The blend ratio of the intended DNA and the first marker gene to be used for the co-transformation is not especially limited, but the ratio is preferably between 3:1-1:5, and more preferably between 2:1-1:3.

Transformation Method

In the present invention, the transformation method is not especially limited as long as it is a method capable of transforming a plant, and an appropriate method can be selected in accordance with the type of plant. For example, a physicochemical method (direct introduction of DNA) such as a particle-gun method, an electroporation method, an electro-injection method, a polyethylene-glycol method or a whisker method, or a biological method (indirect introduction of DNA) such as an *Agrobacterium*-mediated method can be suitably used.

Co-Transformation

Herein, a genetic modification of a cell resulting from introduction and incorporation (and expression) of an exogenous genetic material (exogenous DNA) is designated as transformation. This term is used also for referring to a step (process) performed for the modification. In addition, simultaneous transformation of independent two or more exogenous genetic materials is designated as co-transformation. This term is similarly used also for referring to a step for conducting it. It is noted that "being independent" means that the two or more exogenous genetic materials are introduced into a cell not as an integral DNA but as DNAs respectively capable of independently behaving.

A co-transformation method mediated by *Agrobacterium* is divided into the following four types: A type in which a plurality of T-DNAs are separately located on a plurality of binary vectors in one strain (one-strain multi-vector method); a type in which two T-DNAs are located on one binary vector in one strain (one-strain one-vector method); a type in which two T-DNAs are separately located on binary vectors of two strains and the strains are mixedly inoculated (two-strain method), and a type in which one T-DNA containing two genes obtained by using two right border sequences is located on one binary vector of one strain (Yau and Stewart, 2013). In the present invention, any type of the method can be suitably practiced. As for the two-strain method, the number of strains is not especially limited to two, but a plurality of T-DNAs can be separately located on binary vectors of a plurality of strains to be mixedly inoculated.

It is noted that the fourth type is a method utilizing a double right-border method. This is one of methods for excluding a selectable marker in performing the transformation by the *Agrobacterium*-mediated method (Yau and Stewart, 2013). That is, in this method, a T-DNA is produced to contain "RB (right border sequence)—positive selectable marker—RB—intended DNA—LB (left border sequence)" in this order, and "RB—positive selectable marker—RB—intended DNA—LB" and "RB—intended DNA—LB" are introduced into chromosomes of different plants, so that these can be segregated in the next generation. By applying this method, when a T-DNA is produced to contain "RB—negative selectable marker—RB—positive selectable marker—intended DNA—LB" (or "RB—negative selectable marker—RB—intended DNA—positive selectable marker—LB") in this order and this T-DNA is used for the transformation, "RB—negative selectable marker—RB—intended DNA—positive selectable marker—LB" and "RB—intended DNA—positive selectable marker—LB" are produced, which is the same situation attained by conducting the co-transformation using two T-DNAs. Accordingly, also in this case, transformed cells having a high copy number can be eliminated by applying this method to the method of the present invention. Herein, the transformation using such a T-DNA is included in the co-transformation.

The particle-gun method is a method in which a DNA is introduced into a cell by ejecting, at a high speed, a bullet of a particle of a metal, such as gold or tungsten, coated with the DNA. This method is also designated as a biolistic method, a particle bombardment method or a microprojectile method. As the bullet, a gold particle is preferably used because gold has a high specific gravity, is highly penetrative into a cell, and is chemically inert and difficult to harm a living body. For ejecting a metal particle, a high pressure gas of helium or the like is mainly used. The ejection speed of the metal particle can be adjusted in accordance with the pressure of the gas, a distance between the metal particle and a sample, and the like, and a DNA can be introduced into various cells by this method. In employing the particle-gun method, the co-transformation can be conducted by using, as the bullet, a metal particle coated with two or more DNAs for introducing the DNAs into a cell.

The electroporation method is a method in which the transformation is conducted by applying an electrical pulse to a cell suspension for forming a small hole in a cell membrane, and sending a DNA contained in the cell suspension into the cell. If a plant cell is used as a material, a protoplast in which a cell wall is removed by degradation is generally used. However, the transformation can also be conducted by using a cell having a cell wall, and this method is designated as the electro-injection method. In employing the electroporation method or the electro-injection method, the co-transformation can be conducted by dissolving two or more DNAs in a suspension and applying an electrical pulse in the presence of a plant cell.

In the polyethylene-glycol method, polyethylene glycol (PEG) is caused to act on a protoplast, so as to allow a DNA to be incorporated into a plant cell. The mechanism of this DNA incorporation has not been cleared yet.

A whisker method is a method in which a plant cell is pierced with a needle-like substance designated as a whisker, so as to allow a DNA to be incorporated into the cell. As the whisker, silicon carbide, aluminum borate, or the like is used.

In addition, for the transformation of the intended DNA and the marker gene, the same transformation method may be employed for both, or different transformation methods may be employed for them, but it is more preferable to efficiently employ the same transformation method to conduct the co-transformation.

Second Marker Gene

Further, a positive selectable marker gene may be linked, as a second marker gene, to the intended DNA. In particular, if the intended DNA cannot be used as an index for determining whether or not the transformation has been successfully conducted, namely, if the intended DNA does not have a property as a marker gene, a positive selectable marker gene is preferably linked to the DNA.

The term "positive selection" as used herein refers to selective selection of a cell in which a marker gene is expressed, and a marker gene that can be used for the positive selection is designated as a positive selectable marker gene.

If a marker gene expressing cell and a cell in which a marker gene is not introduced are visually discriminated from each other, the marker gene expressing cell can be artificially removed from a cell group by using a tool such as tweezers or a knife, for example, under a microscope. Accordingly, a gene having a characteristic to give a visually discriminable property such as fluorescence to a cell can be used as the positive selectable marker gene. Examples of such a marker gene include fluorescent protein genes of a green fluorescent protein (GFP), a red fluorescent protein (DsRed), luciferase gene and the like, and a gene of an enzyme catalyzing a color reaction, such as a lacZ gene.

Alternatively, as the positive selectable marker gene, for example, a gene that prevents a phenomenon of a cell such as cell death, cell growth arrest or abnormal tissue formation when integrated and expressed in a plant chromosome genome in a period from the gene transfer process up to the regeneration of a plant can be suitably used. The positive selection can be efficiently performed by setting conditions so that a cell in which such a positive selectable marker gene is expressed can be viable but a cell in which the positive selectable marker gene is not expressed cannot be viable. Examples of the positive selectable marker gene include, but are not limited to, antibiotic resistance genes such as a hygromycin resistance gene, a gentamicin resistance gene, a kanamycin resistance gene, an ampicillin resistance gene, a spectinomycin resistance gene and a tetracycline resistance gene; herbicide resistance genes such as a bialaphos resistance gene and a glyphosate resistance gene; and a gene imparting a new sugar metabolic activity to a plant, such as a phosphomannose isomerase (PMI) gene, a 2-deoxyglucose-6-phosphatase gene or a xylose isomerase gene.

Further, an antibiotic or a herbicide harmfully affects a non-transformed plant cell, but a sugar such as mannose or xylose is not toxic although it is a carbon source non-metabolizable by a plant. Here, a carbon source originally non-metabolizable by a plant is used as a selectable drug to be combined with a selectable marker of an enzyme gene that converts such a carbon source into a carbon source metabolizable by a plant, and thus, a selection system that does not harmfully affect a non-transformed cell is constructed, and in some cases, this system may be designated as a (narrow sense) positive selection system and the selectable marker may be designated as a (narrow sense) positive selectable marker gene (Upadhaya et al., 2010). As described above, however, the positive selection of the present invention refers to the selective selection of a cell in which a marker gene is expressed, and a marker gene usable in the positive selection is referred to as the positive selectable marker gene, and thus, these terms are not limited to the narrow senses.

Accordingly, the present invention includes an embodiment in which a positive selectable marker gene, which is a second marker gene, is linked to the intended DNA used in the step (a), and the selection of the transformed cells with the intended DNA introduced into a chromosome in the step (b) is conducted by positive selection using the second marker gene.

That "a positive selectable marker gene, which is a second marker gene, is linked to the intended DNA" means that the intended DNA and the second marker gene are linked to each other and together behave in the transformation. Accordingly, if the intended DNA is integrated into the chromosome of a plant cell by the transformation, the second marker gene is also integrated. On the other hand, if the transformation fails and the intended DNA is not integrated into the chromosome of a plant cell, the second marker gene is not also integrated. In this respect, the second marker gene is different, in position in the transformation, from the first marker gene that is co-transformed as a DNA separate from and independent of the intended DNA and behaves differently.

Figure 5:
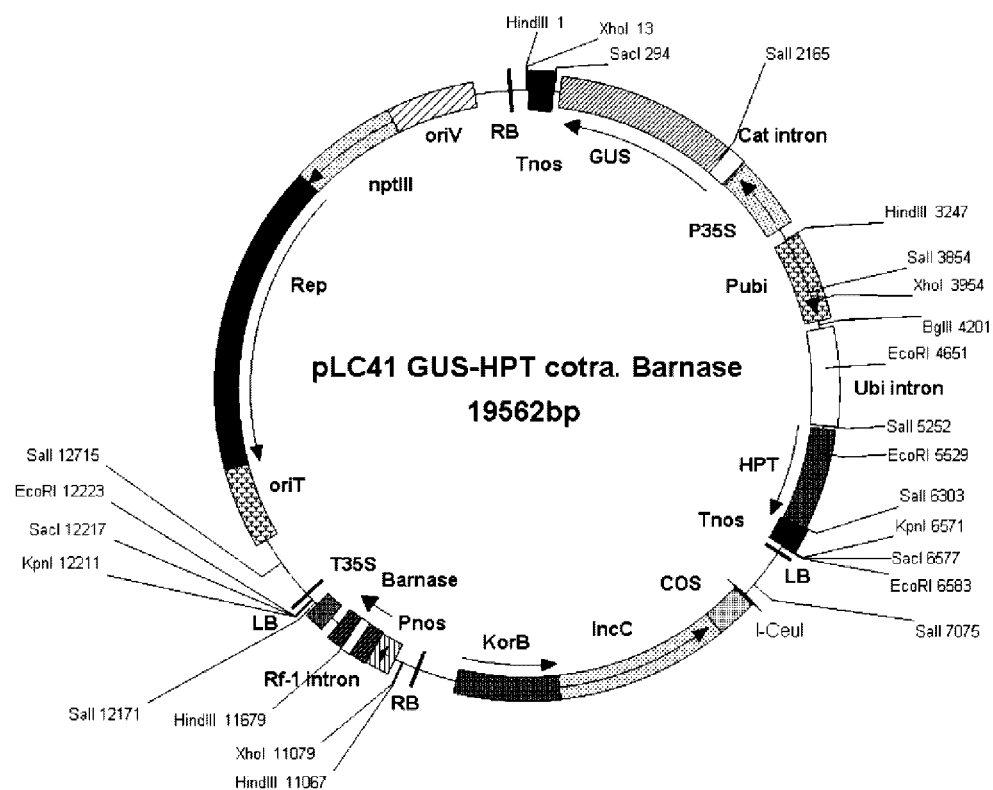
FIG. 5 is a schematic diagram of an expression vector pLC41 GUS-HPT cotra. Barnase.

For example, if the co-transformation is conducted by the type of the *Agrobacterium*-mediated method in which two T-DNAs are located on one binary vector in one strain (the one-strain one-vector method), the intended DNA and the second marker gene are linked to each other to be sandwiched between a pair of "RB" and "LB". For example, "RB—second marker gene—intended DNA—LB". On the other hand, the first marker gene is sandwiched between "RB" and "LB" different from those sandwiching the intended DNA. For example, a sequence is as illustrated in FIG. 5 of the present application. Alternatively, if the double right-border method is employed, a T-DNA may be produced to contain "RB—negative selectable marker—RB—positive selectable marker—intended DNA—LB" (or "RB—negative selectable marker—RB—intended DNA—positive selectable marker—LB").

Selection of Transformed Cell

The term transformed cell as used herein refers to a cell in which a foreign gene has been integrated into the chromosome genome through a transformation process, or a progeny of the cell.

In the step (b) of the present invention, a transformed cell with the intended DNA introduced into a chromosome thereof, and the first marker gene is not introduced, is selected from transformed plant cells obtained in the step (a).

The order of the selection is not especially limited. Specifically, any of the following embodiments can be employed:

1) A transformed cell containing the first marker gene is excluded, and a transformed cell containing the intended DNA is selected from the remaining cells;

2) a transformed cell containing the intended DNA is selected, and a transformed cell containing the first marker gene is excluded from the remaining cells; and 3) exclusion of a transformed cell containing the first marker gene and selection of a transformed cell containing the intended DNA are simultaneously conducted.

For "excluding a transformed cell containing the marker gene", in an embodiment where the first marker gene is, for example, a negative selectable marker gene, a transformed cell containing the marker gene can be excluded by negative selection for causing cell death, cell growth arrest, abnormal tissue formation or the like when the negative selectable marker gene is expressed in the cell where the gene has been introduced into the chromosome thereof.

Also for "selecting a transformed cell containing the intended DNA", if the intended gene is a marker gene, merely a cell having a property based on the expression of the marker gene is selected. If the intended DNA cannot be used as an index for determining whether or not the transformation has been successfully conducted, namely, if the intended DNA is not a marker gene, a positive selectable maker gene is preferably linked to the DNA. Only a cell having a property based on the expression of the positive selectable marker gene is selected.

The expression of each gene of the intended DNA, the first marker gene and the second marker gene may be constitutive or inductive. If the expression is inductive, the gene expression can be induced by, for example, a specific compound externally supplied described later. The inductive expression can be conducted not only by an externally supplied specific compound but also by a stressing treatment such as a high-temperature treatment or a low-temperature treatment.

Furthermore, the selection of a transformed cell does not include selection by using a selectable marker in a transformed plant progeny obtained by crossing transformed plants.

Gene Expression Induction System Using Specific Compound

There is a method for inducing gene expression by an externally supplied compound. In the method of the present invention, the expression time of the selectable marker gene may be controlled by using such a gene expression induction system using a specific compound. In particular, if a strong negative selectable marker gene inducing cell death or cell growth arrest at a transient expression level is used as the first marker gene, it is preferable, from the viewpoint of the transformation efficiency, to put the expression time of the marker gene off till the marker gene is integrated into the chromosome genome. In such a case, any of gene expression induction systems using a specific compound described below can be employed to control the expression time.

Conditions for such a gene expression induction system include: (1) that a specific compound is necessary as an inducer or an activator for controlling the activity of a trans transcription factor, and that such a compound is not synthesized by itself in a life cycle of a plant and has a low possibility of coming into contact with the plant; and (2) that the plant does not contain a cis element of a promoter controlling the transcription. For example, if a cis element of a bacteria or the like, which are evolutionarily distant, is used, there is a low possibility that a trans transcription factor originally contained in the plant is interacted with the cis element. In order satisfy the above-described conditions, a chimeric/trans transcription factor, in which three domains of an amino acid sequence of a domain linked to a bacteria-derived cis sequence, an amino acid sequence of a domain linked to a specific compound for controlling the activity of a transcription factor, and an amino acid sequence of a transcription activation domain, are synthesized. At present, a gene expression induction system using tetracycline, estradiol or the like has been developed.

(i) Tetracycline induction system: The expression of the tetracycline resistance operon (tet operon) on the Tn10 transposon of $E.\ coli$ is negatively regulated by TetR (amino acid sequence) working as a repressor, and tetO (5'-TCCC-TATCAGTGATAGAGAA-3' (SEQ ID NO: 26) working as an operator. In the absence of tetracycline, TetR is linked to tetO to inhibit transcription, but in the presence of tetracycline, it dissociates from tetO. In other words, tetracycline is an inducer of the tet operon. Therefore, the gene tetR of TetR linked to downstream from a promoter of a gene constitutively expressed in a plant is combined with a plurality of tetO linked to downstream from another promoter with a gene desired to be expressed linked to downstream therefrom. If the tetracycline is administered as an inducer, the gene downstream from the tetO is induced. It is noted that doxycycline has higher inducibility as an inducer than tetracycline.

(ii) Estradiol induction system: This is a transcriptional induction system containing a synthesized transcriptional activator XVE (amino acid sequence), which is obtained by fusing amino acid residues in positions 1-87 of LexA, that is, a repressor of SOS regulon of $E.\ coli$, a transcriptionally active site (amino acid residues in positions 403-479) of VP16 (amino acid sequence) derived from herpes simplex virus (HSV) and the regulatory region (amino acid residues in positions 282-595) of human/estrogen receptor, and locating a plurality of SOS boxes (5'-TACTGTATATATA-CAGTA-3') (SEQ ID NO: 27), that is, an operator originally linked to LexA, as a cis sequence linked to XVE, upstream from TATA box of the CaMV 35S minimal promoter. The CaMV 35S minimal promoter has minimum transcriptional activity in the absence of estradiol. If XVE and estradiol are bound to each other, however, XVE binds to an SOS box to strongly induce the transcriptional activity of the CaMV 35S minimal promoter located downstream. In other words, this is a positively regulated system.

Method of Producing Transformed Plant

The present invention further relates to a method of producing a transformed plant. The method of producing a transformed plant of the present invention comprises: obtaining a transformed plant cell by the method of obtaining a transformed plant cell of the present invention; and culturing the plant cell to obtain a plant.

In the method of the present invention, the transformed cell is cultured. In the step of culturing the transformed cell to obtain a plant, an arbitrary method in accordance with the type of plant can be employed.

As a culture medium, for example, a medium based on LS inorganic salts or N6 inorganic salts, such as an LSZ medium, can be used. The culture medium may contain a selectable drug. The "culture" performed in this step means that a plant cell or a plant tissue is placed on a solid culture medium or in a liquid culture medium to be grown at an appropriate temperature under appropriate light-dark condition for an appropriate time period. In the present invention, the form of a medium is not especially limited as long as a medium component can be sufficiently supplied to a plant tissue. The culture medium can be solidified, for example, by using agarose or the like. The culture temperature employed in this step can be appropriately selected, and is preferably 20° C. to 35° C., and more preferably 25° C. Besides, the culture of this step is conducted preferably under light conditions of 16 to 24 hours/day, which does not limit the present invention. The culture period of this step is also appropriately selected, and is preferably 7 to 21 days, and more preferably 14 days.

Method of Transforming Plant

The present invention also relates to a method of transforming a plant. The method of the present invention comprises the steps of:

(a) co-transforming an intended DNA and a first marker gene into a plant cell; and (b) selecting from the transformed cells obtained in the step (a), a transformed plant cell wherein the intended DNA is introduced into a chromosome thereof, and the first marker gene is not introduced, wherein the method does not contain a step to exclude a transformed cell with only the intended DNA introduced into the chromosome by positive selection using the first marker gene.

EXAMPLES

The present invention will now be described on the basis of examples, which do not limit the present invention. A person skilled in the art could easily modify/change the present invention based on the description given herein, and such modifications/changes are also within the technical scope of the present invention.

Example 1

Construction of Co-transformation Vector

1) Target DNA and Positive Selectable Marker Gene

A β-glucuronidase (GUS) gene mediated by the first intron of a castor bean catalase gene was used as a target DNA, and a hygromycin resistance (HPT) gene was used as a positive selectable marker gene. The GUS gene was controlled by a 35S promoter, and nos was used as a terminator. The HPT gene was controlled by a promoter of a maize ubiquitin (Ubi) gene, and nos was used as a terminator. Besides, the first intron of the maize ubiquitin gene was located upstream from the HPT coding region.

2) Negative Selectable Marker Gene

A Barnase gene of *Bacillus amyloliquefaciens* was used as a negative selectable marker gene. The expression was controlled by a nos promoter, and 35S was used as a terminator. Besides, since the expression of Barnase also kills *E. coli* and *Agrobacterium*, the Barnase gene was mediated by the fifth intron of a rice Rf-1 gene (Pnos-Barnase-T35S). As a result, this marker can be changed to a negative selectable marker expressing merely in a plant cell. The sequence in which the Barnase gene of *Bacillus amyloliquefaciens* used was mediated by the fifth intron of the rice Rf-1 gene is set forth in SEQ ID NO: 1, the sequence of the Barnase gene of *Bacillus amyloliquefaciens* is set forth in SEQ ID NO: 2, and the sequence of the fifth intron of the rice Rf-1 gene is set forth in SEQ ID NO: 3. A base sequence of bases at 180-288 in SEQ ID NO: 1 corresponds to a base sequence of the fifth intron of the rice Rf-1 gene of SEQ ID NO: 3.

Figure 2:
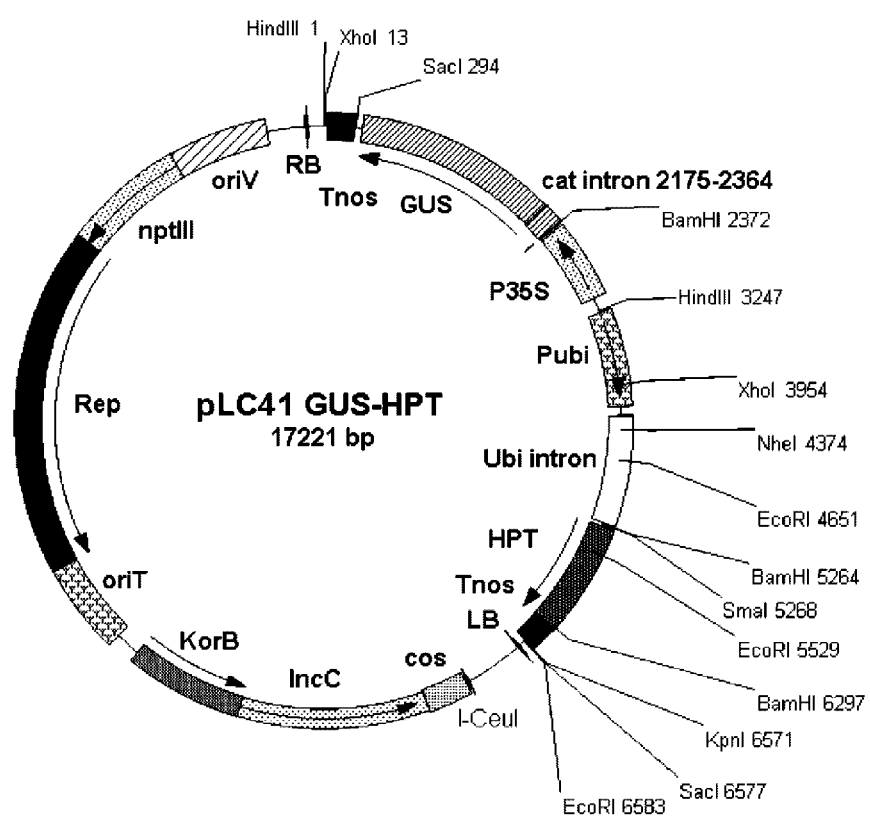
FIG. 2 is a schematic diagram of an expression vector pLC41 GUS-HPT.

3) Construction of Binary Vector pLC41 GUS-HPT (FIG. 2)

Figure 3:
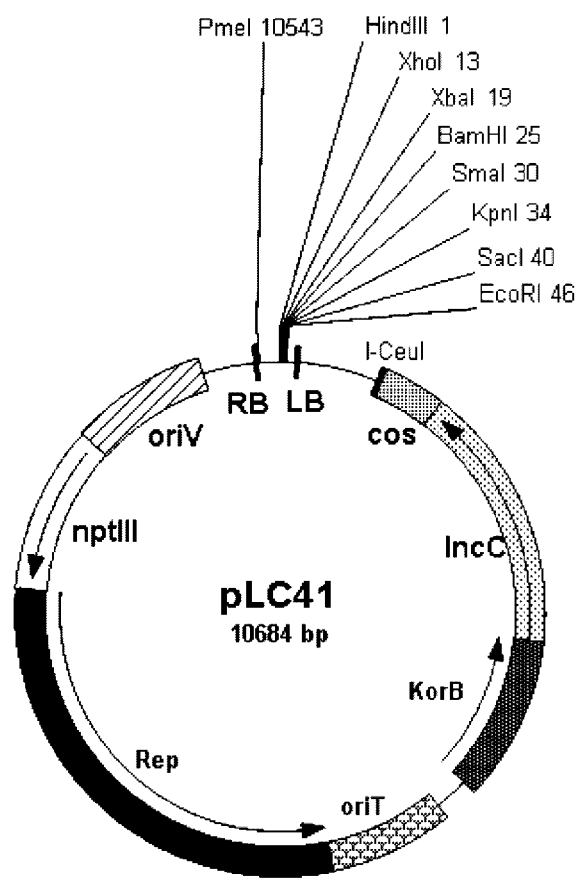
FIG. 3 is a schematic diagram of an expression vector pLC41.

A cosmid vector pLCleo (also designated as pLC41GWH) described in International Publication No. WO 2007/148819 A1 is an IncP plasmid having an origin of replication oriV. The oriV works in both *E. coli* and *Agrobacterium*. An EcoRI-PmeI fragment of pLC41GWH and an EcoRI-PmeI fragment of pSB11 (Komari et al., 1996) having a multi-cloning site are ligated to each other to obtain a binary vector pLC41 (FIG. 3) having a multi-cloning site alone on a T-DNA.

A vector pLC41 GUS-HPT was constructed as follows: First, PCR was conducted for amplifying a GUS-HPT fragment. The PCR was conducted by using pSB34 (Hiei and Komari, 2006) as a template, and by using a primer GUS-HPT in pSB34F, which contains a 3' portion of Tnos positioned downstream from GUS and a sequence encoding SpeI located downstream, and a primer GUS-HPT in pSB34R, which contains a 3' portion of Tons positioned downstream from HPT and a sequence encoding KpnI located downstream. The thus obtained GUS-HPT fragment was double digested with SpeI and KpnI, and ligated to a pLC41 vector precedently double digested with XbaI and KpnI, and thus, the vector pLC41 GUS-HPT was obtained. This vector was introduced into *Agrobacterium* LBA4404 by the electroporation method, resulting in obtaining LBA4404 (pLC41 GUS-HPT) (left in FIG. 1-*b*).

TABLE 1

| pLC41 GUS + HPT related primers | | | |
|---|---|---|---|
| Name | Sequence (5'-3') | Length | SEQ ID NO. |
| GUS-HPT in pSB34 F | GGACTAGTCCGATCTA GTAACATAGATG | 28 mer | 4 |
| GUS-HPT in pSB34 R | TCATGTTTGACAGGGT ACCATCGGATGAG | 29 mer | 5 |

Figure 4:
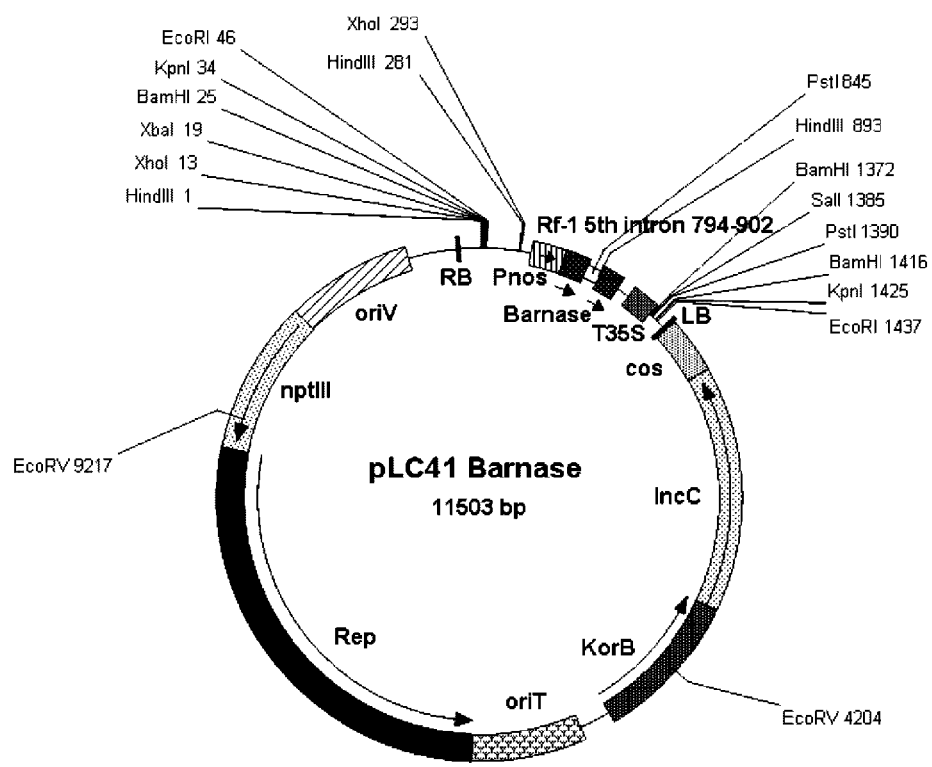
FIG. 4 is a schematic diagram of an expression vector pLC41 Barnase.

4) Construction of Binary Vector pLC41 Barnase (FIG. 4)

A vector pLC41 Barnase was constructed as follows: First, a Pnos-Baranse-T35S fragment (hereinafter referred to as the Barnase fragment) was synthesized to be cloned in an EcoRV site of a pUC57 vector (Barnase/pUC57). Next, the PCR was conducted for amplifying the Barnase fragment. Barnase/pUC57 was used as a template, and as primers, M13/pUC 24 mer encoding an M13 sequencing primer region and pUC57 476 (ArII) long R in which a sequence encoding AvrII is added to a 3' portion of the multi-cloning site of pUC 57 were used. As a result, a PCR product of 1120 bp was obtained. The thus obtained Barnase fragment was TA cloned into a vector pCR4TOPO (manufactured by Invitrogen) to obtain pCR4TOPO/Barnase.

Subsequently, a Barnase fragment was inserted into a multi-cloning site between RB and LB of pLC 41. Specifically, after pLC 41 was digested with XbaI, the resultant was dephosphorylated and ligated with a Barnase fragment of the pCR4TOPO/Barnase precedently digested with SpeI, so as to obtain pLC41 Barnase (FIG. 4). This vector was introduced into *Agrobacterium* LBA4404 by the electroporation method to obtain LBA4404 (pLC41 Barnase) (right in FIG. 1-*b*).

TABLE 2 pLC41 Barnase related primers

| Name | Sequence (5'-3') | Length | SEQ ID NO. |
|---|---|---|---|
| M13/pUC 24 mer | GACGTTGTAAAACGAC GGCCAGTG | 24 mer | 6 |
| pUC57 476 (AvrII) R | GCTATGACCATGATTA CGCCTAGGTTGCAT | 30 mer | 7 |

5) Production of Double T-DNA Binary Vector pLC41 GUS-HPT Cotra. Barnase (FIG. 5)

Next, the PCR was conductor for amplifying RB-Barnase-LB from about 330 bp upstream from RB to about 520 bp downstream from LB by using pLC41 Barnase as a template, and for amplifying pLC41 GUS-HPT KorB to oriT from KorB to oriT by using pLC41 GUS-HPT as a template. In the PCR reaction for RB-Barnase-LB, a 5'-phosphorylated primer (pLC41 330 bp—RB F+P) containing a sequence encoding about 330 bp upstream portion from RB and a 5'-phosphorylate primer (pLC41 LB—520 bp R+P) containing a sequence encoding about 520 bp downstream portion from LB were used. In the PCR reaction for pLC41 GUS-HPT KorB to oriT, a primer pLC41 oriT-IncC F containing a sequence encoding a portion between oriT and IncC in the downstream direction and a primer pLC41 oriT-IncC R containing a sequence encoding the portion between oriT and IncC in the upstream direction were used. As a result, a PCR product of about 2280 bp was obtained for the RB-Barnase-LB fragment, and a PCR product of about 17000 bp was obtained for the pLC41 GUS-HPT KorB to oriT fragment.

The RB-Barnase-LB fragment and the pLC41 GUS-HPT KorB to oriT fragment were ligated to each other to obtain a vector pLC41 GUS-HPT cotra. Barnase (FIG. 5).

This vector was introduced into *Agrobacterium* LBA4404 by the electroporation method to obtain LBA4404 (pLC41 GUS-HPT cotra. Barnase) (FIG. 1-*a*).

TABLE 3 pLC41 GUS-HPT cotra. Barnase related primers

| Name | Sequence (5'-3') | Length | SEQ ID NO. |
|---|---|---|---|
| pLC41 330 bp- RB F + P | p + CGACAAGCAGAT CACGCTTTTCGAC | 25 mer | 8 |
| pLC41 LB- 520 bp R + P | p + CTCCAAGAGACG GTTACACAAACGG | 25 mer | 9 |
| pLC41 oriT- IncC F | TGAATCCGATGCTGTT CTACATCGC | 25 mer | 10 |
| pLC41 oriT- IncC R | TTCTTCGGTCCTCCTT GTAGCGG | 23 mer | 11 |

Figure 7:
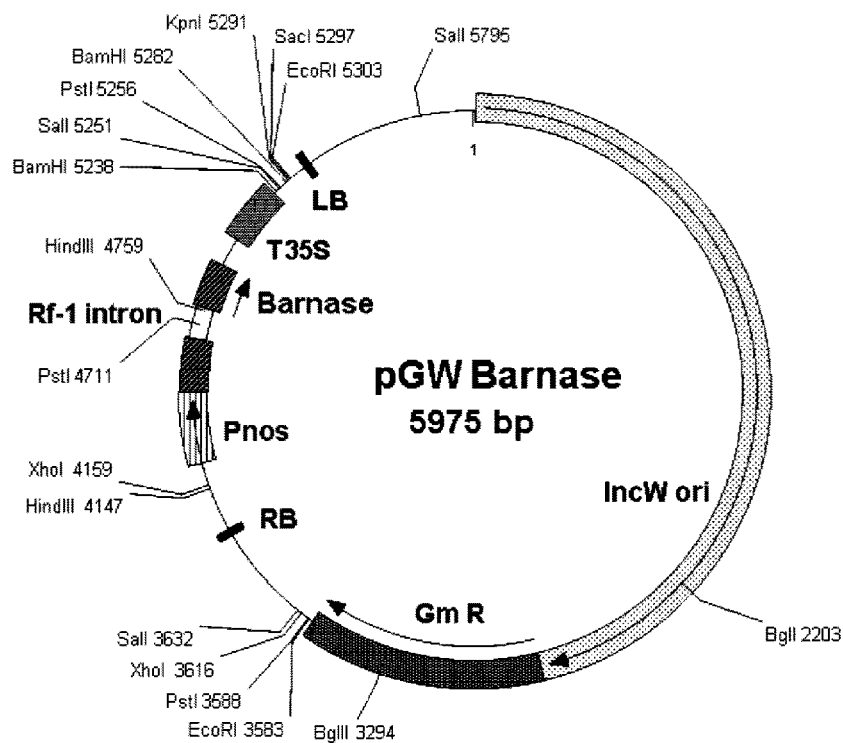
FIG. 7 is a schematic diagram of pGW Barnase.

6) Production of Ternary Vector pGW Barnase (FIG. 7)

Figure 6:
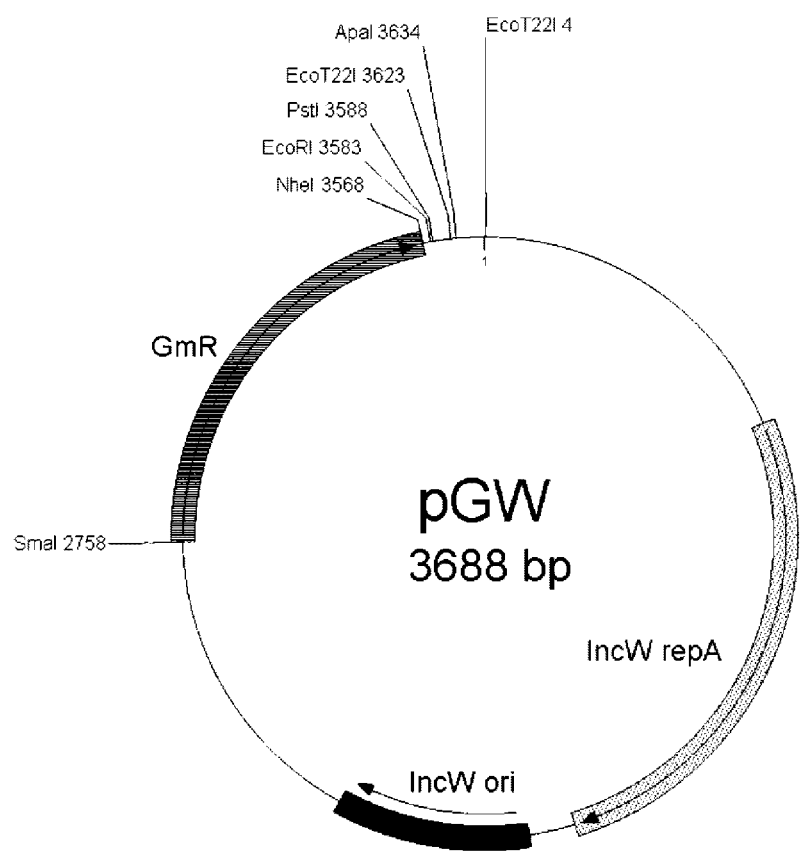
FIG. 6 is a schematic diagram of pGW.

Patent Literature WO2007/148819 A1 discloses a vector pVGW2 (Inc W type) that can coexist with a binary vector pLC41 (Inc P type) in *Agrobacterium* and contains virG N54D derived from pTiBo542. In this example, the vector pVGW2 was modified into a simpler vector pGW (FIG. 6) by removing virG N54D therefrom. Specifically, with pVGW2 used as a template, the PCR was conducted by using a primer set of pSa5'EcT22I and M13 (−20) Fw, and the resultant fragment was self-ligated to obtain a novel cloning vector pGW (FIG. 6) to be used as a ternary vector. The vector pGW can be retained in the same *Agrobacterium* together with the second vector (binary vector) pLC41 as a third vector (ternary vector), and a T-DNA can be located with respect to each of these vectors. Accordingly, a target DNA linked to a positive selectable marker gene and a negative selectable marker can be co-transformed by using merely one type of *Agrobacterium* (FIG. 1-*c*). By using pLC41 Barnase as a template, the PCR was conducted for adding an SpeI site to each of both ends of an RB-Barnase-LB cassette. In the PCR reaction, a primer pLC41 330 bp—RB+SpeI F (10 pmol/ul) having a sequence containing an SpeI site added to 330 bp upstream from the RB and a primer pLC41 520 bp—LB+SpeI R having a sequence containing an SpeI site added to 520 bp downstream from the LB were used. As a result, an SpeI fragment of RB-Barnase-LB was obtained as a PCR product of 2300 bp. This fragment was ligated to pGW precedently digested with XbaI, and thus, pGW Barnase in which the RB-Barnase-LB fragment was inserted in a forward direction was obtained.

The thus completed pGW Barnase was introduced into *Agrobacterium* LBA4404 simultaneously with pLC41 GUS-HPT by the electroporation to obtain LBA4404 (pLC41 GUS-HPT::pGW Barnase) (FIG. 1-*c*).

TABLE 4 pGW Barnase related primers

| Name | Sequence (5'-3') | Length | SEQ ID NO. |
|---|---|---|---|
| pSa5'EcT221 | AAAATGCATGGCATGT TTAACAGAATCTG | 29 mer | 12 |
| M13(-20)Fw | GTAAAACGACGGCCA | 15 mer | 13 |

Example 2

Transformation of Rice Using Co-Transformation Vector System

Materials and Method

1) Tested *Agrobacterium* Strain and Vector

The following three types of co-transformation vector systems for eliminating multicopy cells were used for conducting the co-transformation of a target DNA linked to a positive selectable marker gene, and a negative selectable marker gene.

a. One-strain one-vector type: LBA4404 (pLC41 GUS-HPT cotra. Barnase) (FIG. 1-*a*)

b. Two-strain mixed type: LBA4404 (pLC41 GUS-HPT)+ LBA4404 (pLC41 Barnase) (FIG. 1-*b*)

c. One-strain two-vector type: LAB4404 (pLC41 GUS-HPT::pGW Barnase) (ternary vector system) (FIG. 1-c)

2) Transformation Method for Rice

As a variety of rice, Yukihikari was used. Ears of the rice greenhouse cultured were collected on about the 10th day after flowering. After sterilizing immature seeds from which glumes had been excluded with tweezers, immature embryos having a length of 1.3 to 1.8 mm were collected under stereomicroscope. These immature embryos were subjected to centrifugation at centrifugal acceleration of 20,000×g for 10 minutes. *Agrobacterium* was cultured on AB medium (Chilton et al., 1974) supplemented with a selectable drug in accordance with the drug resistance of the strain at 28° C. under dark conditions for 3 days, and thereafter suspended in 1.0 ml AA-inf medium (AA major inorganic salts, B5 minor inorganic salts, B5 vitamin, AA amino acid, 0.1 mM acetosyringone, 20 g/l sucrose, 10 g/l glucose, 0.5 g/l vitamin assay casamino acid, pH 5.2). The suspension concentration was adjusted to about 1.0 in terms of an OD value at 660 nm. Besides, if two strains were mixedly inoculated, both the strains were adjusted to have an OD value of about 1.0, and then mixed to be inoculated. Next, the immature embryos were placed, with the scutellum facing upward, on N6-As medium for cocultivation (N6 inorganic salts and vitamin, 1 mg/l 2,4-D, 0.5 mg/l 6BA, 20 g/l sucrose, 10 g/l glucose, 0.5 g/l proline, 0.5 g/l vitamin assay casamino acid, 8 g/l agarose type I, 0.1 mM acetosyringone, pH 5.2), and the *Agrobacterium* suspension was added dropwise thereto. The cocultivation was conducted at 25° C. under dark conditions for 7 days.

After the cocultivation, each of the immature embryos was cut into 4 to 6 sections, and placed, with the scutellum facing upward, on nN6C medium (N6 inorganic salts and vitamin, 1 mg/l 2,4-D, 0.5 mg/l 6BA, 20 g/l sucrose, 55 g/l sorbitol, 0.5/l proline, 0.5 g/l vitamin assay casamino acid, 5 g/l gellan gum, 250 mg/l cefotaxime, 100 mg/l carbenicillin, pH 5.8) to be non-selectively (resting) cultured at 30° C. under light conditions of 5,000 1× for 10 days. Each section of the immature embryos was further cut into 4 to 5 sections, and placed on nN6CH50 selective medium (N6 inorganic salts and vitamin, 1 mg/l 2,4-D, 0.5 mg/l 6BA, 20 g/l sucrose, 55 g/l sorbitol, 0.5 g/l proline, 0.5 g/l vitamin assay casamino acid, 5 g/l gellan gum, 250 mg/l cefotaxime, 100 mg/l carbenicillin, 50 mg/l hygromycin B, pH 5.8) to be selectively cultured by using hygromycin at 30° C. under light conditions of 5,000 1× for 10 to 14 days.

Proliferated calluses were placed on N6RH50 regeneration medium (N6 minor inorganic salts and vitamin, ½ concentration N6 major inorganic salts, AA amino acid, 0.5 mg/l kinetin, 20 g/l sucrose, 30 g/l sorbitol, 0.5 g/l vitamin assay casamino acid, 4 g/l gellan gum, 50 mg/l hygromycin B, pH 5.8), and cultured at 30° C. under light conditions of 5,000 1× for 14 days. The number of calluses to be placed on the regeneration medium was one per a single piece of immature embryo section. Therefore, the respective calluses placed on the regeneration medium can be dealt with as independent transformation events. Regenerated seedlings were transplanted in N6FH50 rooting medium (N6 minor inorganic salts and vitamin, ½ concentration N6 major inorganic salts, AA amino acid, 20 g/l sucrose, 0.5 g/l vitamin assay casamino acid, 4 g/l gellan gum, 50 mg/l hygromycin B, pH 5.8), and cultured at 30° C. under light conditions of 5,000 1× for 10 to 14 days. Each rooted plant was transplanted to a pot and cultured in a greenhouse.

3) Southern Analysis of Transformed Rice Plant

Figure 8:
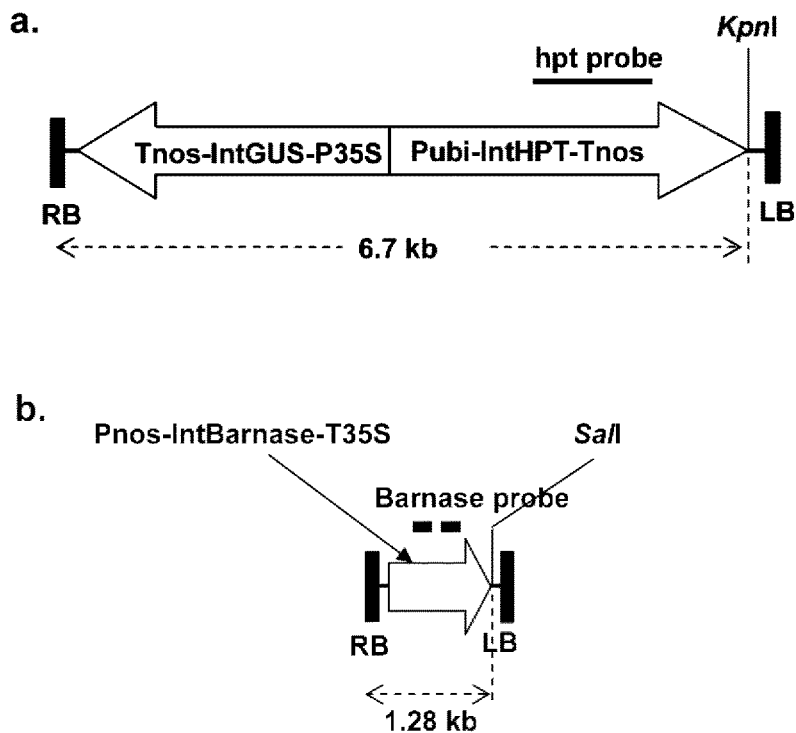
FIG. 8 is a schematic diagram of two introduced T-DNAs, in which a. illustrates a T-DNA region common to pLC41 GUS-HPT cotra. Barnase and pLC41 GUS-HPT, and b. indicates a T-DNA region common to pLC41 GUS-HPT::pGW Barnase, pLC41 Barnase and pGW Barnase.

A genomic DNA was extracted from a leaf of the hygromycin-resistant transformant cultured in the greenhouse by phenol-chloroform extraction method. After digesting the genomic DNA with KpnI, agarose electrophoresis was conducted in a TAE buffer by using Type II agarose (SIGMA). After performing the transfer to a nylon membrane by alkaline blotting, southern hybridization was conducted by using hpt as a probe (FIG. 8-*a*). Besides, 51 transformed rice plants obtained by using LBA4404 (pLC41 GUS-HPT cotra. Barnase) (FIG. 1-*a*) of the one-strain one-vector type were digested with SalI and then subjected to southern analysis by using Barnase as a probe (FIG. 8-*b*).

Result and Discussion

1) Result of Transformation of Rice

Transformants were obtained in all the experimental plots, but the transformation efficiency was lower in an experimental plot in which Barnase was co-transformed as compared with a control plot in which GUS-HPT alone was introduced (Table 5). This is because Barnase used as a negative selectable marker was integrated together with GUS-HPT into the chromosome of the same rice cell, and the cell was killed by the expression of Barnase. The cell death of rice caused by Barnase appears in the form of obvious browning partially caused in cells on the scutellum surface. The browning starts to be observed on 10 to 20 days after inoculating *Agrobacterium*. This is prior to the start of the selective culture, and hence the browning is not caused by the influence of hygromycin. Besides, immediately after the cocultivation of 7 days, the transient GUS activity in a scutellum cell of an immature embryo is not prevented, and when treated with a solution of 5-bromo-4-chloro-3-indolyl-β-D-glucuronic acid (X-Gluc), that is, a substrate, equivalent GUS activity was exhibited in the control and three types of experimental plots. This reveals that Barnase does not kill a cell at the transient expression level.

When LBA4404 (pLC41 GUS-HPT cotra. Barnase) of the one-strain one-vector method was used, the efficiency was lowered by 30% (Table 5). The transformation efficiencies attained by the two-strain mixed inoculation method of LBA4404 (pLC41 GUS-HPT) and LBA4404 (pLC41 Barnase) and the one-strain two-vector method of LBA4404 (pLC41 GUS-HPT::pGW Barnase) were equivalent and were both 90% or more (Table 5). This reveals that the introduction efficiency of both the T-DNAs into the same cell was high in the one-strain one-vector method. This is probably because the two T-DNAs are cut at substantially the same timing in a large number to be transferred to plant cells in the one-strain one-vector method as compared with the other experimental plots. Besides, if Barnase induces cell death at the transient expression level, the transformation efficiency is presumed to be extremely low. Since such a result was not obtained, it seems that the expression of Barnase was suitably controlled by the nos promoter.

TABLE 5

Transformation efficiency in rice variety of Yukihikari

| Tested vector system | Number of tested immature embryos (a) | Number of hygromycin-resistant plants (independent events) (b) | Efficiency (b/a) | Efficiency comparison (control = 100) |
|---|---|---|---|---|
| Control | 70 | 836 | 11.9 | 100 |
| One-strain one vector | 60 | 494 | 8.2 | 69 |
| Two-strain mixed | 40 | 435 | 10.9 | 91 |
| One-strain two-vector | 20 | 223 | 11.2 | 93 |

* Control: LBA4404 (pLC41 GUS-HPT)
One-strain one-vector: LBA4404 (pLC41 GUS-HPT cotra. Barnase)
Two-strain mixed: LBA4404 (pLC41 GUS-HPT) + LBA4404 (pLC41 Barnase)
One-strain two-vector: LBA4404 (pLC41 GUS-HPT::pGW Barnase)

2) Analysis of Number of Introduced Copies by Southern Method

Figure 9:
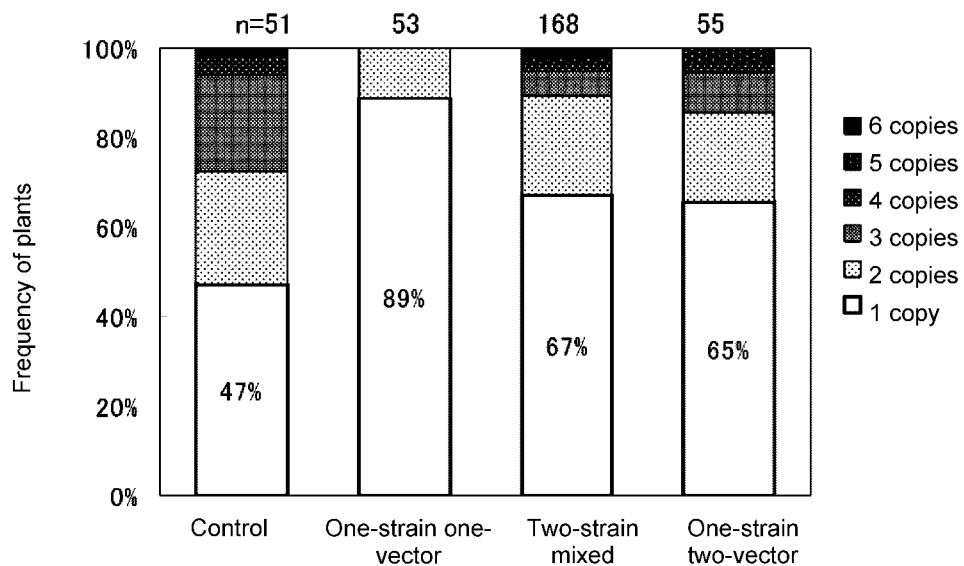
FIG. 9 is a diagram illustrating the introduced copy number of a GUS-HPT fragment estimated as a result of Southern analysis, in which Control: LBA4404 (pLC41 GUS-HPT), One-strain one-vector: LBA4404 (pLC41 GUS HPT cotra. Barnase), Two-strain mixed: LBA4404 (pLC41 GUS-HPT)+LBA4404 (pLC41 Barnase), and One-strain two-vector: LBA4404 (pLC41 GUS-HPT::pGW Barnase).

A result of the southern hybridization performed by using an hpt probe is illustrated in FIG. 9. At least one of bands detected from each of the analyzed transformants had a size of 6.7 kb or more. The detection of a band of 6.7 kb or more suggests that the whole T-DNA of GUS-HPT is introduced. While single copy introduction was attained in 47% of the analyzed plants in using a control vector, the single copy introduction was attained in 89% of the plants, which is twice or more as many, in using the one-strain one-vector system. Besides, in all the remaining 11% of the plants, the number of introduced copies was 2 (FIG. 9). In using the two-strain mixed system and the one-strain two-vector system, ratios of single copy plants were substantially the same, and were respectively 67% and 65%, which were 1.43 times and 1.38 times as many as that attained in using the control (FIG. 9). In this manner, the ratio of low copy number transgenic plants was remarkably increased in the experimental plots, which reveals that the Barnase gene used as the negative selectable marker tends to be introduced together if GUS-HPT is introduced at a high copy number into the chromosome of one cell in the co-transformation. Wang and Waterhouse (2000) have reported that T-DNAs repeatedly linked to one another in the forward or mutually reverse direction are integrated into the same locus in many of transformed rice plants obtained by the *Agrobacterium*-mediated method. It is presumed that a cell producing such a transformed plant is killed in the co-transformation with a negative selectable marker gene.

The southern hybridization using a Barnase probe was conducted on the 51 transformed rice plants obtained by using LBA4404 (pLC41 GUS-HPT cotra. Barnase) of the one-strain one-vector method. In all the plants, any signal hybridizing with the Barnase gene were not detected. It was found that the introduced Pnos-IntBaranse-TS35S was expressed necessarily and sufficiently for inducing the cell death of the plant. It is presumed that Barnase induces the cell death even expressed at a slight expression level.

3) Conclusion

It was found that a multicopy transgenic cell can be eliminated at an initial stage of cultivation by the co-transformation of a negative selectable marker gene and a target DNA containing a positive selectable marker gene. Although the three types of *Agrobacterium* vector systems were used in this example, these systems are not restrictive but it is easily presumed that a wide range of transformation systems can be employed. It is obvious, in consideration of the mechanism, that the direct introduction of DNA such as the particle-gun method can be applied to the co-transformation. In the direct introduction, the multicopy introduction originally frequently occurs, and hence, this method is extremely effective for reducing the copy number.

Example 3

Elimination of Multicopy Transformant of Tobacco by Co-Transformation Using Barnase Materials and Method 1) Transformation of Tobacco The seeds of a tobacco variety, SR1, were sterilized with antiformin, and aseptically sowed on rooting medium (½ concentration LS inorganic salt, ½ concentration LS vitamin, 15 g/l sucrose, 3 g/l gellan gum, 250 mg/l cefotaxime, pH 5.8). After sowing, the resultant was cultured at 25° C. under light conditions to be grown until cotyledons were fully opened. A rectangular cotyledon segment obtained by cutting, with scissors, the tip and base of a fully opened cotyledon was used for infection with *Agrobacterium*. The inoculation of *Agrobacterium* was conducted by collecting cotyledon segments on LSR liquid medium (LS inorganic salt, LS vitamin, 30 g/l sucrose, 0.5 g/l 4-morpholineethanesulfonic acid (MES) monohydrate (pH 5.8) in a dish, replacing the liquid medium with an *Agrobacterium* suspension, and immersing the segments therein for 10 minutes. The *Agrobacterium* suspension was prepared by culturing *Agrobacterium* on AB medium supplemented with 50 mg/l kanamycin at 28° C. under dark conditions for 3 days, and suspending the resultant in LSR liquid medium. The suspension concentration was adjusted to 1.0 in terms of an OD value at 660 nm. The test was conducted in two experimental plots, that is, a control plot in which LBA4404 (pLC41 GUS-HPT) was singly inoculated, and an experimental plot in which two strains of LBA4404 (pLC41 Barnase) and LBA4404 (pLC41 GUS-HPT) were mixedly inoculated.

After inoculating *Agrobacterium*, the leaf segments were placed on LSR solid medium supplemented with 3 g/L gellan gum with the underside of the segment facing upward, and cocultured at 25° C. under dark conditions for 2 days. After the cocultivation, the leaf segments were transplanted in LS-S medium (LS inorganic salt, LS vitamin, 10 mg/l 6-(γ,γ-dimethylallylamino)purine (2ip), 0.3 mg/l indole-3-acetic acid (IAA), 30 g/l sucrose, 250 mg/l cefotaxime, pH 5.8), and cultured at 28° C. under light conditions for 2 to 4 days. Next, the resultant was transplanted in LS-S medium supplemented with 50 mg/l hygromycin for selecting hygromycin-resistant cells. A hygromycin-resistant shoot obtained at the cut end of each leaf segment was cut off from the leaf segment, and transplanted in rooting medium supplemented with 50 mg/l hygromycin and 250 mg/l cefotaxime. The thus obtained rooted plant was transplanted in a culture vessel having a large capacity (77 mm in length, 77 mm in width and 97 mm in height) containing a medium having the same medium composition, and cultured until sampling. The thus obtained hygromycin-resistant plant was used as a transformant in the following analysis.

2) Measurement of Copy Number of Introduced DNA in Transformed Tobacco Plant by Quantitative Real Time PCR For measuring the copy number of T-DNA integrated in the transformed tobacco plant, quantitative real time PCR was employed. Multiplex PCR in which a target DNA region and an internal standard DNA region are amplified in the same well was employed. The target DNA region was set within an HPT gene. From a leaf of each transformed plant, a genomic DNA was extracted by using E. Z. N. A. (registered trademark) SP Plant DNA Kit (Omega Bio-Tek), and was prepared to a concentration of 12.5 ng/μl. Three cycles of the real time PCR were repeatedly conducted in a 96-well PCR plate by using Applied Biosystems (registered trademark) 7500 Real Time PCR System (Life Technologies Corporation), and this PCR was conducted twice. A PCR reaction solution contained 25 μl Premix Ex. Taq (TaKaRa), 5 μl template DNA, 0.3 to 0.4 μM primer, and 0.2 to 0.24 μM Taq Man MGB probe (Life Technologies Corporation), and the total amount was set to 50 μl. The PCR primer and the Taq Man MGB probe were designed by Primer Express (Life Technologies Corporation). The names of the designed primer and probe are mentioned below, and their sequences are shown in Table 6. As internal standard primers, NtBWC1-5F and NtBWC1-5R were used, and as an internal standard Taq Man MGB probe, NtBWC1-5P was used. As primers for a target DNA, Hpt-2F and Hpt-2R were used, and as a Taq Man MGB probe for the target DNA, Hpt-2P was used. All the real time PCR experiments were conducted in accordance with the following program: 95° C. for 30 seconds once, followed by 40 times of 95° C. for 5 seconds and 60° C. for 34 seconds. Fluorescence was monitored in an extension step at 60° C. of each cycle.

For evaluation of the efficiency of the quantitative PCR analysis and relative quantification, a calibration curve was created by serial dilutions of five concentrations (36, 18, 9, 4.5 and 2.25 ng/μl) of the genomic DNA. A threshold line was measured as 0.06, and a baseline was measured as 3 to 16 cycles. The copy number was calculated in accordance with a method of Yang et al., (2005).

TABLE 6

Primers and Taq Man MGB probes used in quantitative real time PCR

| Name | Sequence (5'-3') | Length | SEQ ID NO. |
|---|---|---|---|
| NtBWC1-5F | GTGTCTCCGGCGGTGAAC | 18 mer | 14 |
| NtBWC1-5R | ATCGGGTCATGGATTATGTCAAT | 23 mer | 15 |
| Hpt-2F | GGATTTCGGCTCCAACAATG | 20 mer | 16 |
| Hpt-2R | GCCTCGCTCCAGTCAATGAC | 20 mer | 17 |
| NtBWC1-5P | VIC-CGCGTTTCAATCGG-MGB | 14 mer | 18 |
| Hpt-2P | FAM-CCTGACGGACAATGGCCGCATAAC-MGB | 24 mer | 19 |

Result and Discussion

1) Result of Transformation of Tobacco

As compared with the control plot where GUS-HPT alone was introduced, the transformation efficiency was lowered to about ⅓ in the experimental plot where the Barnase gene was co-transformed by the two-strain mixed method (Table 7). It seems that the transformation efficiency was lowered because the Barnase gene used as the negative selectable marker was integrated together with the GUS-HPT gene in the genome of the same cell of tobacco and hence the cell was killed by stable expression of Barnase. In the experimental plot, at the stage where the selection was conducted in the LS-S medium supplemented with hygromycin, the efficiency of forming a hygromycin-resistant shoot from a leaf segment was lowered to about ⅓. Therefore, the labor to transplant a shoot in the rooting medium and to prepare the rooting medium was largely reduced.

The co-transformation of rice was conducted by the two-strain mixed method in Example 2, and the lowering of the transformation efficiency was as small as about 10%. It seems that the transformation efficiency was remarkably lowered in the case of tobacco because the efficiency of integrating two T-DNAs in the genome of the same cell, namely, the co-transformation efficiency, is higher than in rice.

TABLE 7

Result of transformation of tobacco SR1

| Experimental plot | Number of inoculated leaf segments (a) | Number of independent transformed plants (b) | Transformation efficiency per leaf segment (b/a: %) | Efficiency comparison (control = 100) |
|---|---|---|---|---|
| Control* | 137 | 118 | 86.1% | 100 |
| Test (two-strain mixed)** | 135 | 41 | 30.4% | 35 |

*Control: LBA4404(pLC41 GUS-HPT)
**Test (two-strain mixed): LBA4404(pLC41 GUS-HPT) + LBA4404(pLC41 Barnase)

Figure 10:
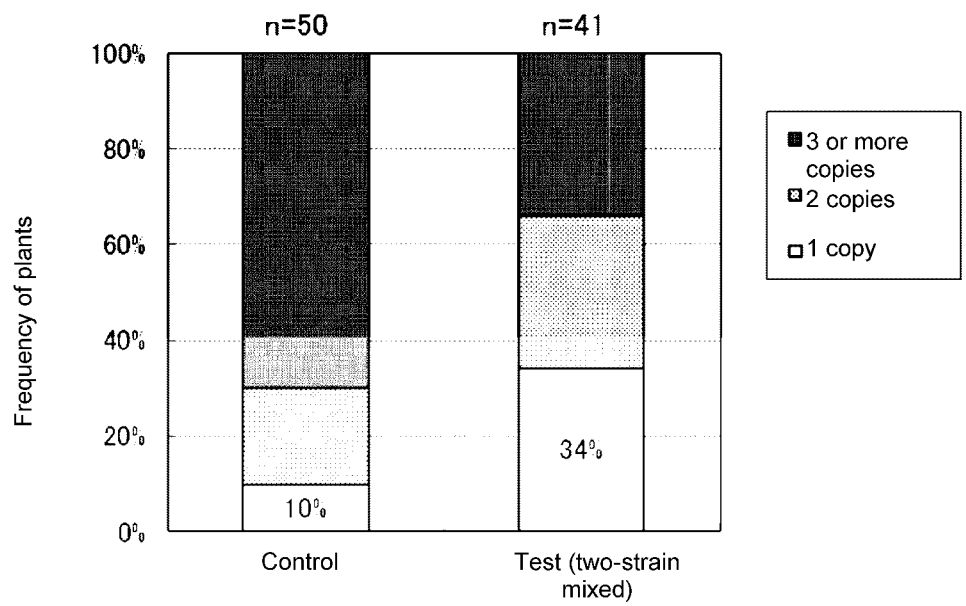
FIG. 10 is a diagram illustrating the introduced copy number of a GUS-HPT fragment in a transformed tobacco plant estimated by quantitative real time PCR, in which Control: LBA4404 (pLC41 GUS-HPT), and Test (two-strain mixed): LBA4404 (pLC41 GUS-HPT)+LBA4404 (pLC41 Barnase).

2) Analysis of Copy Number of Introduced DNA in Transformed Tobacco Plant by Quantitative Real Time PCR The copy number of DNA introduced into tobacco was analyzed by the quantitative real time PCR. The result is illustrated in FIG. 10. In the control plot where LBA4404 (pLC41 GUS-HPT) was singly inoculated, GUS-HPT was introduced as a single copy in 10% of the analyzed plants, and at a high copy number in the remaining 90%. On the contrary, in the experimental plot where the Barnase gene was co-transformed by the two-strain mixed inoculation method, GUS-HPT was introduced as a single copy in 34% of plants, which is as three times as many as that in the control plot (FIG. 10). On the other hand, the ratio of plants in which GUS-HPT was introduced at a copy number of 3 or more was largely reduced (FIG. 10). This is because the Barnase gene used as a negative selectable marker is easily introduced together if GUS-HPT, that is, the target gene, is introduced at a high copy number into the same genome, and hence such a cell is eliminated at an early stage of the cultivation by the expression of Barnase.

As described so far, the ratio of the transformed tobacco plants containing a single copy of the target gene was increased by three or more times in the experimental plot. On the other hand, the transformation efficiency was lower to about ⅓. Since multicopy transgenic cells can be eliminated at an early stage of the cultivation, however, the labor to perform the cultivation and the cost and labor to prepare a medium could be largely reduced. As a conclusion, it was confirmed that the method of co-transforming a negative selectable marker is, in general, a useful technique by which a transformant containing a single copy of a target gene can be efficiently obtained.

Example 4

Elimination of Multicopy Transformant of Maize by Co-Transformation Using Barnase Materials and Method 1) Transformation of Maize Immature embryos of maize (variety: A188) with a size of about 1.2 mm were aseptically taken out from greenhouse cultured plants, and were immersed in liquid medium LS-inf (Ishida et al., 2007). After performing a heat treatment at 46° C. for 3 minutes, the resultant immature embryos were washed once with the liquid medium, and then subjected to centrifugation at 20,000 G for 10 minutes (at 4° C.). The inoculation of *Agrobacterium* was conducted by immersing the immature embryos in an *Agrobacterium* suspension. The thus obtained *Agrobacterium* adhering immature embryos were placed on LS-AS cocultivation medium (Ishida et al., 2007) and cultured at 25° C. under dark conditions for 3 days. The *agrobacterium* suspension was prepared by culturing *Agrobacterium* on YP medium at 28° C. under dark conditions for 2 days and suspending the resultant in LS-inf-As liquid medium supplemented with 0.1 mM acetosyringone. The suspension concentration was adjusted to 1.0 in terms of an OD value at 660 nm. The test was conducted in two experimental plots, namely, in a control plot in which LBA4404 (pSB131) (Ishida et al., 1996) was singly inoculated, and an experimental plot in which two strains of LBA4404 (pSB131) and LBA4404 (pLC41 Barnase:: pVGW9) obtained by introducing a super-ternary vector pVGW9 (Patent Literature WO2014-157541A1) into LBA4404 (pLC41 Barnase) were mixedly inoculated. The vector pSB131 is a super-binary vector, and contains, in its T-DNA, an intron-GUS gene controlled by the 35S promoter and a bar gene controlled by the 35S promoter. The bar gene is a phosphinothricin (PPT) resistance gene.

After the cocultivation, the immature embryos were placed on LSD1.5B selection medium with 5 mg/l PPT (Ishida et al., 2007) and subjected to primary selection at 25° C. under dark conditions for 10 days. The thus proliferated calluses were directly transplanted in LSD1.5B selection medium supplemented with 10 mg/l PPT and subjected to secondary selection for about 3 weeks. The calluses proliferated through the secondary selection were cut into small pieces, and subjected to tertiary selection for about 3 weeks in a medium having the same composition. The calluses proliferated through the tertiary selection were cut into small pieces, placed on LSZ regeneration medium (Ishida et al., 2007) supplemented with 5 mg/l PPT, and cultured at 25° C. under light conditions. Two weeks after, a PPT-resistant regenerated plant was transplanted in LSF rooting medium (Ishida et al., 2007) supplemented with 5 mg/l PPT, and cultured under the same conditions until sampling. The thus obtained PPT-resistant plant was used as a transformant in the following analysis.

2) Measurement of Copy Number of Introduced DNA in Transformed Maize Plant by Quantitative Real Time PCR For measuring the copy number of T-DNA integrated in a transformed maize plant, the quantitative real time PCR was used. The multiplex PCR in which a target DNA region and an internal standard DNA region are amplified in the same well was employed. The target DNA region was set within a bar gene. From the leaf of each transformant, a genomic DNA was extracted by using E. Z. N. A. (registered trademark) SP Plant DNA Kit, and was prepared to a concentration of 15.625 ng/µl. Three cycles of the real time PCR were repeatedly conducted in a 96-well PCR plate by using Applied Biosystems (registered trademark) 7500 Real Time PCR System, and this PCR was conducted twice. A PCR reaction solution contained 25 µl Premix Ex. Taq, 5 µl template DNA, 0.3 µM primer, and 0.2 µM Taq Man MGB probe, and the total amount was set to 50 µl. The PCR primer and the Taq Man MGB probe were designed by Primer Express. The names of the designed primer and probe are mentioned below, and their sequences are shown in Table 8.

TABLE 8

Primers and Taq Man MGB probes used in quantitative real time PCR

| Name | Sequence (5'-3') | Length | SEQ ID NO. |
|---|---|---|---|
| Hmg-2F | CCTCTCCTGGTCGAACTTTTCA | 22 mer | 20 |
| Hmg-2R | GACTCGCTCAGGGATTTCCA | 20 mer | 21 |
| Bar-1F | ACAGCGACCACGCTCTTGA | 19 mer | 22 |
| Bar-1R | GCTCTACACCCACCTGCTGAA | 21 mer | 23 |
| Hmg-2P | VIC-AAAGCTGCTGGCGACAG-MGB | 17 mer | 24 |
| Bar-1P | FAM-CCCTGTGCCTCCAGG-MGB | 15 mer | 25 |

As internal standard primers, Hmg-2F and Hmg-2R were used, and as an internal standard Taq Man MGB probe, Hmg-2P was used. As primers for a target DNA, Bar-1F and Bar-1R were used, and as a Taq Man MGB probe for the target DNA, Bar-1P was used. All the real time PCR experiments were conducted in accordance with the following program: 95° C. for 30 seconds once, followed by 40 times of 95° C. for 5 seconds and 60° C. for 34 seconds. Fluorescence was monitored in an extension step at 60° C. of each cycle. For evaluation of the efficiency of the quantitative PCR analysis and relative quantification, a calibration curve was created by serial dilutions of five concentrations (48, 24, 12, 6 and 3 ng/µl) of the genomic DNA. The copy number was calculated in accordance with the method of Yang et al., (2005).

Result and Discussion

1) Result of Transformation of Maize

As compared with the control plot where GUS-bar alone was introduced, the transformation efficiency was lowered to about ⅔ in the experimental plot in which the Barnase gene was co-transformed by the two-strain mixed method (Table 9). It seems that the transformation efficiency was lowered because the Barnase gene used as the negative selectable marker was integrated together with the GUS-bar gene into the genome of the same maize cell and hence the cell was killed by stable expression of the Barnase. In the experimental plot, a ratio of immature embryos having produced PPT-resistant calluses was lowered to about ⅔ at the end of the secondary selection. Therefore, the labors to cut small pieces of calluses to transplant them in the tertiary selection medium, to transplant the small pieces of the calluses resulting from the tertiary selection in the regeneration medium, and to transplant a regenerated plant in a rooting medium was reduced by ⅓. Since such labor occupies 85% of the whole labor in the transformation of maize, 28% of the labor was thus reduced.

TABLE 9

Result of transformation of maize A188

| Experimental plot | Number of inoculated immature embryos (a) | Number of independent transformed plants (b) | Transformation efficiency per immature embryo (b/a: %) | Efficiency comparison (control = 100) |
|---|---|---|---|---|
| Control* | 550 | 197 | 35.8% | 100 |
| Test (two-strain mixed)** | 629 | 132 | 21.1% | 68 |

*Control: LBA4404(pSB131)
**Test (two-strain mixed): LBA4404(pSB131) + LBA4404(pLC41 Barnase::pVGW9)

Figure 11:
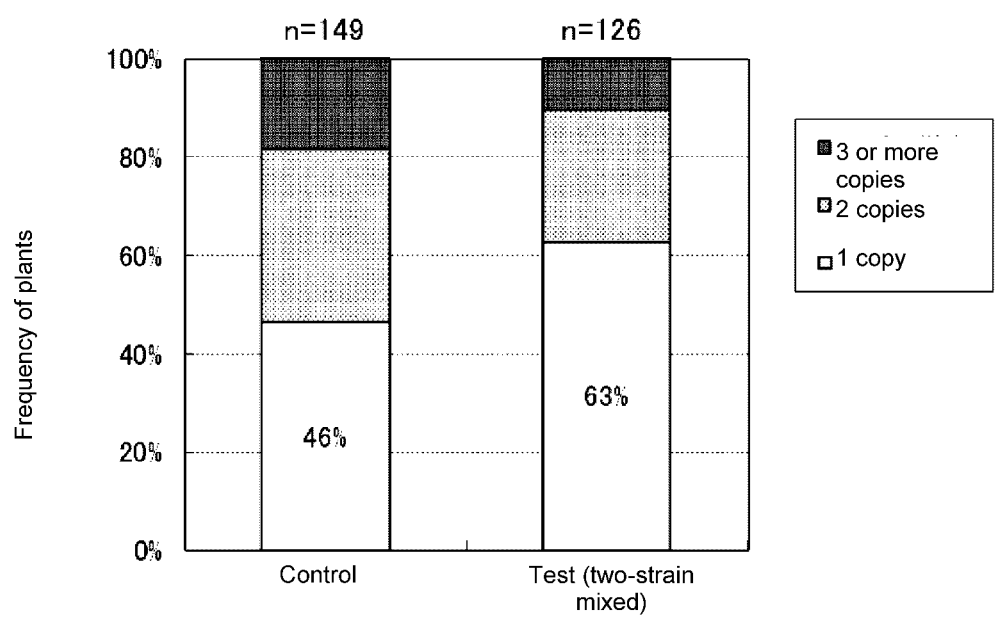
FIG. 11 is a diagram illustrating the introduced copy number of a GUS-bar fragment in a transformed maize plant estimated by the quantitative real time PCR, in which Control: LBA4404 (pSB131), and Test (two-strain mixed): LBA4404 (pSB131)+LBA4404 (pLC41 Barnase::pVGW9).

2) Analysis of Copy Number of Introduced DNA in Transformed Maize Plant by Quantitative Real Time PCR The copy number of DNA introduced into maize was analyzed by the quantitative real time PCR. The result is illustrated in FIG. 11. In the control plot where LBA4404 (pSB131) was singly inoculated, GUS-bar was introduced as single copy in 46% of the analyzed plants, and at a high copy number in the remaining 54%. On the contrary, in the experimental plot where the Barnase gene was co-transformed by the two-strain mixed inoculation method, GUS-bar was introduced as single copy in 63% of plants, which is more by 17% than that attained in the control plot (FIG. 11). On the other hand, a ratio of plants in which GUS-HPT was introduced at a copy number of two or more was 37%, which is reduced by 17% (FIG. 11). This is because the Barnase gene used as the negative selectable marker is easily introduced together if GUS-bar, that is, the target gene, is introduced at a high copy number in the same genome, and hence such a cell is eliminated at an early stage of the cultivation by the expression of Barnase.

In this manner, in the experimental plot, a ratio of transformed maize plants containing a single copy of the target gene was increased by 1.3 or more times as compared with that in the control plot. On the other hand, the transformation efficiency was lowered to about ⅔. Since multi-copy transgenic cells can be eliminated at an early stage of the cultivation, however, the labor to perform the cultivation and the cost and labor to prepare a medium can be largely reduced in the case of maize in the same manner as in the case of tobacco of Example 3. Thus, also for maize, the method of co-transforming a negative selectable marker is, in general, a useful technique by which a transformant containing a single copy of a target gene can be efficiently obtained.

The invention claimed is:

1. A method of obtaining a transformed plant cell, the method comprising the steps of:
   (a) co-transforming, via *Agrobacterium*-mediated transformation, an intended DNA, a positive selectable marker gene, which is a second marker gene linked to the intended DNA, and a first marker gene into a plant cell, wherein the intended DNA and the second marker gene are sandwiched between a pair of RB (right border sequence) of T-DNA and LB (left border sequence) of T-DNA, and the first marker gene is sandwiched between another pair of RB and LB which is different from those sandwiching the intended DNA and the second marker gene;
   (b) selecting from the transformed cells obtained in the step (a), before generation of a first generation plant transformant, a transformed plant cell wherein the intended DNA is introduced into a chromosome thereof, and the first marker gene is not introduced, and
   (c) selecting, from the transformed cells with the intended DNA introduced into a chromosome in the step (b), a transformed plant cell by conducting positive selection using the second marker gene,
   wherein the first marker gene is a negative selectable marker gene,
   wherein the method does not contain a step for selecting a transformed cell with the intended DNA introduced into the chromosome by any positive selection except for the positive selection using the second marker gene.

2. The method of claim 1, wherein a blend ratio of the intended DNA and the first marker gene used for co-transformation in the step (a) is between 3:1-1:5.

3. A method of producing a transformed plant, the method comprising
   obtaining a transformed plant cell by the method described in claim 1;
   culturing the plant cell to obtain a plant.

4. The method of claim 1, wherein the transformed plant cell has a single copy of the intended DNA.

* * * * *

SEQUENCE LISTING

```
<160> NUMBER OF SEQ ID NOS: 27

<210> SEQ ID NO 1
<211> LENGTH: 541
<212> TYPE: DNA
<213> ORGANISM: Artificial Sequence
<220> FEATURE:
<223> OTHER INFORMATION: Barnase gene of Bacillus amyloliquefaciens plus
      No.5 intron of Rf-1 gene of rice

<400> SEQUENCE: 1
atggcacagg ttatcaacac gtttgacggg gttgcggatt atcttcagac atatcataag     60
ctacctgata attacattac aaaatcagaa gcacaagccc tcggctgggt ggcatcaaaa    120
gggaaccttg cagacgtcgc tccggggaaa agcatcggcg gagacatctt ctcaaacagg    180
taatttattt ggccatacct acaccagaga tccatatatt acttttataa ctgcagtttt    240
tacttgttaa catttcattg tgcttttaca tttgttccaa gctttcaggg aaggcaaact    300
cccgggcaaa agcggacgaa catggcgtga agcggatatt aactatacat caggcttcag    360
aaattcagac cggattcttt actcaagcga ctggctgatt tacaaaacaa cggaccatta    420
tcagaccttt acaaaaatca gataacgaaa aaaacgqctt cctgcqqaqq ccqtttttt     480 cagctttaca taaagtgtgt aataaatttt tcttcaaact ctgatcggtc aatttcactt    540
t                                                                    541

<210> SEQ ID NO 2
```

```
<211> LENGTH: 432
<212> TYPE: DNA
<213> ORGANISM: Bacillus amyloliquefaciens

<400> SEQUENCE: 2
atggcacagg ttatcaacac gtttgacggg gttgcggatt atcttcagac atatcataag      60
ctacctgata attacattac aaaatcagaa gcacaagccc tcggctgggt ggcatcaaaa     120
gggaaccttg cagacgtcgc tccggggaaa agcatcggcg agacatctt ctcaaacagg      180 gaaggcaaac tcccgggcaa aagcggacga acatggcgtg aagcggatat taactataca     240
tcaggcttca gaaattcaga ccggattctt tactcaagcg actggctgat ttacaaaaca     300
acggaccatt atcagacctt tacaaaaatc agataacgaa aaaaacggct tcctgcggag     360
gccgtttttt tcagctttac ataaagtgtg taataaattt ttcttcaaac tctgatcggt     420
caatttcact tt                                                         432

<210> SEQ ID NO 3
<211> LENGTH: 109
<212> TYPE: DNA
<213> ORGANISM: rice

<400> SEQUENCE: 3
gtaatttatt tggccatacc tacaccagag atccatatat tactttata actgcagttt      60 ttacttgtta acatttcatt gtgcttttac atttgttcca agctttcag                109

<210> SEQ ID NO 4
<211> LENGTH: 28
<212> TYPE: DNA
<213> ORGANISM: Artificial Sequence
<220> FEATURE:
<223> OTHER INFORMATION: GUS-HPT in pSB34 F primer

<400> SEQUENCE: 4
ggactagtcc gatctagtaa catagatg                                        28

<210> SEQ ID NO 5
<211> LENGTH: 29
<212> TYPE: DNA
<213> ORGANISM: Artificial Sequence
<220> FEATURE:
<223> OTHER INFORMATION: GUS-HPT in pSB34 R primer

<400> SEQUENCE: 5
tcatgtttga cagggtacca tcggatgag                                       29

<210> SEQ ID NO 6
<211> LENGTH: 24
<212> TYPE: DNA
<213> ORGANISM: Artificial Sequence
<220> FEATURE:
<223> OTHER INFORMATION: M13/pUC 24mer primer

<400> SEQUENCE: 6
gacgttgtaa aacgacggcc agtg                                            24

<210> SEQ ID NO 7
<211> LENGTH: 30
<212> TYPE: DNA
<213> ORGANISM: Artificial Sequence
<220> FEATURE:
<223> OTHER INFORMATION: pUC57 476(AvrII) R

<400> SEQUENCE: 7
```

-continued

```
gctatgacca tgattacgcc taggttgcat                                30
```

<210> SEQ ID NO 8
<211> LENGTH: 25
<212> TYPE: DNA
<213> ORGANISM: Artificial Sequence
<220> FEATURE:
<223> OTHER INFORMATION: pLC41 330bp-RB F primer

<400> SEQUENCE: 8

```
cgacaagcag atcacgcttt tcgac                                     25
```

<210> SEQ ID NO 9
<211> LENGTH: 25
<212> TYPE: DNA
<213> ORGANISM: Artificial Sequence
<220> FEATURE:
<223> OTHER INFORMATION: pLC41 LB-520bp R

<400> SEQUENCE: 9

```
ctccaagaga cggttacaca aacgg                                     25
```

<210> SEQ ID NO 10
<211> LENGTH: 25
<212> TYPE: DNA
<213> ORGANISM: Artificial Sequence
<220> FEATURE:
<223> OTHER INFORMATION: pLC41 oriT-IncC F primer

<400> SEQUENCE: 10

```
tgaatccgat gctgttctac atcgc                                     25
```

<210> SEQ ID NO 11
<211> LENGTH: 23
<212> TYPE: DNA
<213> ORGANISM: Artificial Sequence
<220> FEATURE:
<223> OTHER INFORMATION: pLC41 oriT-IncC R primer

<400> SEQUENCE: 11

```
ttcttcggtc ctccttgtag cgg                                       23
```

<210> SEQ ID NO 12
<211> LENGTH: 29
<212> TYPE: DNA
<213> ORGANISM: Artificial Sequence
<220> FEATURE:
<223> OTHER INFORMATION: pSa5'EcT22I primer

<400> SEQUENCE: 12

```
aaaatgcatg gcatgtttaa cagaatctg                                 29
```

<210> SEQ ID NO 13
<211> LENGTH: 15
<212> TYPE: DNA
<213> ORGANISM: Artificial Sequence
<220> FEATURE:
<223> OTHER INFORMATION: M13(-20)Fw primer

<400> SEQUENCE: 13

```
gtaaaacgac ggcca                                                15
```

<210> SEQ ID NO 14
<211> LENGTH: 18
<212> TYPE: DNA

```
<213> ORGANISM: Artificial Sequence
<220> FEATURE:
<223> OTHER INFORMATION: NtBWC1-5F primer

<400> SEQUENCE: 14
gtgtctccgg cggtgaac                                                   18

<210> SEQ ID NO 15
<211> LENGTH: 23
<212> TYPE: DNA
<213> ORGANISM: Artificial Sequence
<220> FEATURE:
<223> OTHER INFORMATION: NtBWC1-5R primer

<400> SEQUENCE: 15
atcgggtcat ggattatgtc aat                                             23

<210> SEQ ID NO 16
<211> LENGTH: 20
<212> TYPE: DNA
<213> ORGANISM: Artificial Sequence
<220> FEATURE:
<223> OTHER INFORMATION: Hpt-2F primer

<400> SEQUENCE: 16
ggatttcggc tccaacaatg                                                 20

<210> SEQ ID NO 17
<211> LENGTH: 20
<212> TYPE: DNA
<213> ORGANISM: Artificial Sequence
<220> FEATURE:
<223> OTHER INFORMATION: Hpt-2R primer

<400> SEQUENCE: 17
gcctcgctcc agtcaatgac                                                 20

<210> SEQ ID NO 18
<211> LENGTH: 14
<212> TYPE: DNA
<213> ORGANISM: Artificial Sequence
<220> FEATURE:
<223> OTHER INFORMATION: NtBWC1-5P primer

<400> SEQUENCE: 18
cgcgtttcaa tcgg                                                       14

<210> SEQ ID NO 19
<211> LENGTH: 24
<212> TYPE: DNA
<213> ORGANISM: Artificial Sequence
<220> FEATURE:
<223> OTHER INFORMATION: Hpt-2P primer

<400> SEQUENCE: 19
cctgacggac aatggccgca taac                                            24

<210> SEQ ID NO 20
<211> LENGTH: 22
<212> TYPE: DNA
<213> ORGANISM: Artificial Sequence
<220> FEATURE:
<223> OTHER INFORMATION: Hmg-2F primer

<400> SEQUENCE: 20
cctctcctgg tcgaactttt ca                                              22
```

<210> SEQ ID NO 21
<211> LENGTH: 20
<212> TYPE: DNA
<213> ORGANISM: Artificial Sequence
<220> FEATURE:
<223> OTHER INFORMATION: Hmg-2R primer

<400> SEQUENCE: 21
gactcgctca gggatttcca                                              20

<210> SEQ ID NO 22
<211> LENGTH: 19
<212> TYPE: DNA
<213> ORGANISM: Artificial Sequence
<220> FEATURE:
<223> OTHER INFORMATION: Bar-1F primer

<400> SEQUENCE: 22
acagcgacca cgctcttga                                               19

<210> SEQ ID NO 23
<211> LENGTH: 21
<212> TYPE: DNA
<213> ORGANISM: Artificial Sequence
<220> FEATURE:
<223> OTHER INFORMATION: Bar-1R primer

<400> SEQUENCE: 23
gctctacacc cacctgctga a                                            21

<210> SEQ ID NO 24
<211> LENGTH: 17
<212> TYPE: DNA
<213> ORGANISM: Artificial Sequence
<220> FEATURE:
<223> OTHER INFORMATION: Hmg-2P primer

<400> SEQUENCE: 24
aaagctgctg gcgacag                                                 17

<210> SEQ ID NO 25
<211> LENGTH: 15
<212> TYPE: DNA
<213> ORGANISM: Artificial Sequence
<220> FEATURE:
<223> OTHER INFORMATION: Bar-1P primer

<400> SEQUENCE: 25
ccctgtgcct ccagg                                                   15

<210> SEQ ID NO 26
<211> LENGTH: 20
<212> TYPE: DNA
<213> ORGANISM: Artificial Sequence
<220> FEATURE:
<223> OTHER INFORMATION: terO (operator)

<400> SEQUENCE: 26
tccctatcag tgatagagaa                                              20

<210> SEQ ID NO 27
<211> LENGTH: 20
<212> TYPE: DNA
<213> ORGANISM: Artificial Sequence
<220> FEATURE:

```
<223> OTHER INFORMATION: SOS boxes

<400> SEQUENCE: 27
tactgtatat atatacagta                                                         20
```